United States Patent [19]

Kadin

[11] Patent Number: 4,725,616
[45] Date of Patent: Feb. 16, 1988

[54] 1,3-DICARBOXAMIDO - OXINDOLES AS ANTIINFLAMMATORY AGENTS

[75] Inventor: Saul B. Kadin, New London, Conn.

[73] Assignee: Pfizer Inc., New York, N.Y.

[21] Appl. No.: 8,105

[22] Filed: Jan. 20, 1987

Related U.S. Application Data

[63] Continuation-in-part of Ser. No. 753,200, Jul. 9, 1985, abandoned.

[51] Int. Cl.$^4$ .................. A61K 31/405; C07D 209/34
[52] U.S. Cl. ..................................... 514/411; 514/414; 514/418; 546/256; 546/273; 548/181; 548/233; 548/245; 548/246; 548/336; 548/431; 548/466; 548/467; 548/468; 548/486
[58] Field of Search ................ 514/418, 411; 548/486, 548/431

[56] References Cited

U.S. PATENT DOCUMENTS

| | | | |
|---|---|---|---|
| 3,190,889 | 6/1965 | Shen | 260/319 |
| 3,632,587 | 1/1972 | Hollowood | 548/486 X |
| 3,634,453 | 1/1972 | McManus et al. | 260/325 |

OTHER PUBLICATIONS

El-Enany et al., Bulletin of the Faculty of Pharmacy (Cairo University), 14, (1975), pp. 29–36.

*Primary Examiner*—Joseph Paul Brust
*Attorney, Agent, or Firm*—Peter C. Richardson; Lawrence C. Akers; J. Trevor Lumb

[57] ABSTRACT

1,3-Dicarboxamidooxindoles as antiinflammatory agents prepared by reaction of the 1-carbamoyloxindole with an isocyanate or by aminolysis of the corresponding alkyl 1-carbamoyloxindole-3-carboxylate.

12 Claims, No Drawings

1,3-DICARBOXAMIDO - OXINDOLES AS ANTIINFLAMMATORY AGENTS

CROSS-REFERENCE TO RELATED APPLICATION

This application is a continuation in part of application Ser. No. 753,200, filed July 9, 1985, now abandoned.

BACKGROUND OF THE INVENTION

Rheumatoid arthritis, which affects 3–4% of the population, is characterized by inflammation and pain of joints. While the etiology of rheumatoid arthritis is not completely understood, both steroid and non-steroidal antiinflammatory therapy has been used to alleviate the symptoms of this illness. It is to this latter class of non-steroidal antiinflammatory agents that the compounds of the present invention relate.

The potent non-steroidal antiinflammatory agent, piroxicam, 4-hydroxy-2-methyl-N-(2-pyridyl)-2H-1,2-benzothiazine-3-carboxamide 1,1-dioxide was reported in U.S. Pat. No. 3,591,584. More recently, antiinflammatory activity was reported in non-steroidal oxindole-3-carboxamides, U.S. Pat. No. 3,634,453.

SUMMARY OF THE INVENTION

In accordance with the instant invention, it has now been found that a group of novel 1,3-dicarboxamidooxindoles are useful as analgesic and antiinflammatory agents. More specifically, the novel compounds of this invention are of the formula

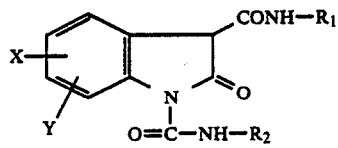

and a pharmaceutically-acceptable base salt thereof, wherein

X is hydrogen, fluoro, chloro, bromo, alkyl of one to four carbon atoms, alkylthio of one to four carbon atoms, alkoxy of one to four carbon atoms, cycloalkyl of three to six carbon atoms, nitro, trifluoromethyl, acyl of two to four carbon atoms, benzoyl or thenoyl;

Y is hydrogen, fluoro, chloro, bromo, alkyl of one to four carbon atoms, alkoxy of one to four carbon atoms or alkylthio of one to four carbon atoms;

X and Y when taken together are 4,5-, 5,6- or 6,7-methylenedioxy; and $R_1$ and $R_2$ are each hydrogen, alkyl of one to six carbon atoms, cycloalkyl of three to seven carbon atoms, heterocyclic or methylated heterocyclic wherein said heterocyclic is pyridyl, thienyl, furyl, pyrrolyl, thiazolyl, oxazolyl, imidazolyl or isoxazolyl, phenyl, substituted phenyl of the formula

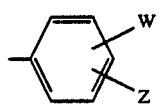

wherein W is hydrogen, fluoro, chloro, bromo, alkyl of one to four carbon atoms, alkylthio of one to four carbon atoms, alkoxy of one to four carbon atoms, acyl of two to four carbon atoms, trifluoromethyl or cycloalkyl of three to six carbon atoms and Z is hydrogen, fluoro, chloro, bromo, alkyl of one to four carbon atoms, alkoxy of one to four carbon atoms or alkylthio of one to four carbon atoms, furylmethyl or thienylmethyl The first preferred group of compounds are those wherein $R_1$ is phenyl or substituted phenyl of the formula

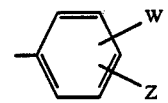

wherein W is hydrogen, fluoro, chloro, bromo, alkyl of one to four carbon atoms, alkylthio of one to four carbon atoms, alkoxy of one to four carbon atoms, trifluoromethyl, acyl or cycloalkyl of three to six carbon atoms and Z is hydrogen, fluoro, chloro, bromo, alkyl of one to four carbon atoms, alkoxy of one to four carbon atoms or alkylthio of one to four carbon atoms; and $R_2$ is hydrogen.

Especially preferred within the first group are those compounds wherein X is 5-chloro, Y is hydrogen and $R_1$ is phenyl, 3-trifluoromethylphenyl 2-chlorophenyl, 2,4-dichlorophenyl or 4-ethylphenyl. Also preferred within this first group are compounds wherein $R_1$ is 2,4-dichlorophenyl and X and Y are each hydrogen or X is 5-chloro and Y is 6-chloro, and wherein $R_1$ is 4-chlorophenyl, X is 6-trifluoromethyl and Y is hydrogen.

A second class of preferred compounds are those wherein $R_1$ is heterocyclic or methylated heterocyclic wherein said heterocyclic is pyridyl, thienyl, furyl, pyrrolyl, thiazolyl, oxazolyl, imidazolyl or isoxazolyl and $R_2$ is hydrogen.

Especially preferred within this second group is the compound wherein $R_1$ is 2-thienyl, X is 5-chloro and Y is hydrogen.

Also included as part of the instant invention is a method of treating an inflammatory disease in a mammalian subject, which comprises administering to said subject an inflammatory disease treating amount of a compound selected from those of the present invention.

In addition, the instant invention comprises a pharmaceutical composition, which comprises a pharmaceutically-acceptable carrier and a compound selected from those of the present invention, and wherein the weight-ratio of the pharmaceutically-acceptable carrier to said compound is in the range of from 1:4 to 20:1.

Also contemplated as part of the present invention are compounds of the following formulae:

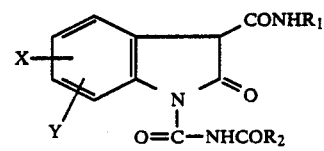

and

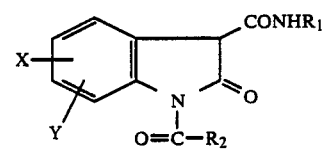

wherein $R_1$, X and Y are as previously defined.

DETAILED DESCRIPTION

One of the processes employed in the preparation of the novel compounds of this invention consists of the interaction of an appropriate oxindole derivative with a requisite isocyanate as follows:

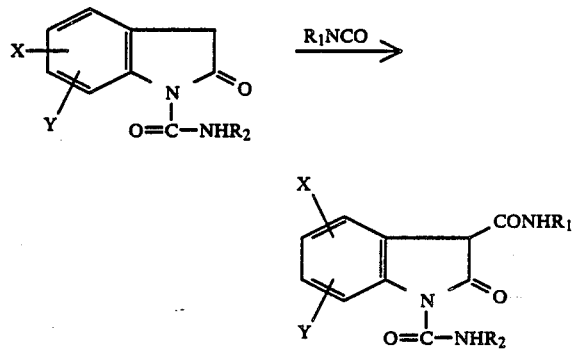

wherein $R_1$, $R_2$, X and Y are as previously defined.

This reaction leading to the products of the instant invention is carried out in a reaction-inert solvent. Preferred solvents are polar, aprotic solvents such as dimethylformamide, diethylformamide, N-methyl-2-pyrrolidone or dimethylsulfoxide. Further, it is preferred that the reaction be carried out in the presence of a base. Such bases include alkali and alkaline earth metal hydrides or a tertiary organic amine. The preferred base is triethylamine.

In practice, the isocyanate is added to the oxindole derivative and base in the appropriate solvent. It is preferable to employ about a molar equivalent of the isocyanate and two molar equivalents of base, with best results achieved by using an excess of as much as 20% of isocyanate and 140% of base. It is preferred that the reagents be combined in the cold, generally from $-5°$ to $0°$ C., and that the reaction mixture be allowed to stir at these temperatures for from one to four hours. The reaction can be allowed to warm to room temperature, in which case the reaction is complete in 30–60 minutes.

Upon completion the reaction can be added to water and acidified to a pH of 2 to 5 using an acid such as hydrochloric acid, or the reaction mixture can be added directly to a 1N solution of hydrochloric acid.

The filtered product can be purified by recrystallization from an appropriate solvent or solvents, or by chromatography.

A second reaction leading to the novel compounds of the present invention consists of the interaction of an appropriate amine with an oxindole, as follows:

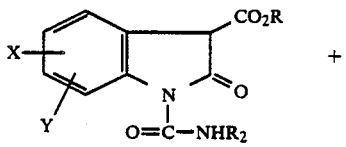 +

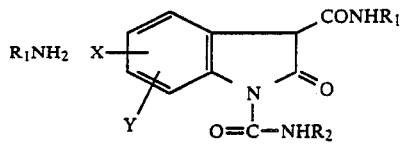

wherein $R_1$, $R_2$, X and Y are as previously defined, and R is alkyl of one to four carbon atoms.

This reaction leading to the products of the present invention is also carried out in a reaction-inert solvent. Preferred solvents are aprotic aromatic solvents such as benzene, toluene or xylene.

In practice, the reagents are combined in the appropriate solvent and heated to the reflux temperature of the solvent. It is preferable, in conducting this aminolysis reaction, to employ at least equimoles of ester and amine, although a 100% molar excess of the amine is especially preferred. To assist in removal of the alcohol by-product formed in the reaction a soxhlet containing molecular sieves is fitted to the reaction condenser. Using reflux temperatures of the solvents, the reaction is generally complete in 1 to 12 hours.

The product can be isolated by cooling the reaction mixture and filtering the product or by adding the reaction mixture to an acidified aqueous solution followed by filtration or extraction of the product and removal of the solvent.

Purification can be carried out by recrystallization or chromatography.

The oxindole starting reagents for these processes are prepared by methods known to those skilled in the art and by the herein described procedures. The requisite isocyanates are either commercially available or can be prepared by standard procedures known in the art, for instance, Zook and Wagner, Synthetic Organic Chemistry, John Wiley and Sons, Inc., New York, 1956, page 640.

It is noted that a common characteristic of many non-steroidal antiinflammatory agents is their acidic nature. Each of the oxindole carboxamides of the instant invention shares this property and is an effective proton source.

Pharmaceutically acceptable salts of the compounds of the present invention are also therapeutic agents, wherein the preferred cations of said salts include the ammonium, sodium and potassium ions. The pharmaceutically acceptable salts of the compounds described herein are prepared by conventional procedures, as for example, by adding the acid to an aqueous solution containing an equivalent amount of the pharmaceutically acceptable base, i.e., a base containing one of the above preferred cations, followed by concentration of the resultant mixture to obtain the desired product. The bases can be selected from hydroxides, oxides or carbonates.

Also considered part of the present invention are 3-enol ethers and acyl ester prodrugs of the herein described compounds. These prodrugs, which have fewer gastrointestinal side effects, breakdown in situ to the parent compound.

As previously indicated, the oxindole-1,3-dicarboxamides of the present invention and their pharmaceutically acceptable salts are useful antiinflammatory agents. These compounds are of value in alleviating swelling and inflammation which are symptomatic of rheumatoid arthritis and related disorders which are responsive to treatment with antiinflammatory agents. Either as individual therapeutic agents or as mixtures of therapeutic agents, they may be administered alone, but are generally administered with a pharmaceutical carrier selected on the basis of the chosen route of administration and standard pharmaceutical practice. For example, they may be administered orally in the form of tablets or capsules containing such excipients as starch, milk sugar or certain types of clay, etc. They may be administered orally in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitably buffered, if necessary, and should contain other solutes such as saline or glucose to render them isotonic. The weight-ratio of the pharmaceutically-acceptable carrier to compound can be from 1:4 to 20:1.

The dosage required to reduce inflammation or swelling in arthritic subjects would be determined by the nature and extent of the symptoms. Generally, small doses will be required initially, with a gradual increase in the dose until the optimum level is determined. It will generally be found that when the composition is administered orally, larger amounts of the active ingredient will be required to produce the same level as produced by a smaller quantity administered parenterally. In general, from about 1.0 to about 30 mg. of active ingredient per kilogram of body weight, administered orally in single or multiple dose units, will effectively reduce inflammation and swelling. Parenteral administration requires doses of from about 0.5 to about 20 mg. per kilogram of active ingredient to achieve the same end point.

A standard procedure for detecting and comparing antiinflammatory activity of compounds is the carrageenin rat foot edema test, which is described by C. A. Winter et al., Proc. Soc. Exp. Biol., vol. III, page 544 (1962).

In addition to being useful as antiinflammatory agents, the compounds of the present invention can be used in the treatment of asthma, bronchitis and psoriasis; they can also used as analgesic agents.

The following examples are provided solely for the purpose of further illustration.

EXAMPLE 1

1-Carbamoyloxindole-3-N-(2,4-dichlorophenyl)carboxamide

To a solution of 1.0 g. (0.0057 mole) of 1-carbamoyloxindole and 1.9 ml. (0.0136 mole) of triethylamine in 25 ml. of dimethylformamide cooled to 0°-5° C. was added 1.28 g. (0.0068 mole) of 2,4-dichlorophenylisocyanate, and the resulting reaction mixture allowed to stir at 0°-5° C. for one hour. To the resulting reaction mixture was added 300 ml. of 1N hydrochloric acid and the mixture allowed to stir for 20 minutes. The product was filtered, dried and recrystallized from acetonitrile, 50 mg., m.p. 227° C. dec.

Anal. Calcd. for $C_{16}H_{11}O_3Cl_2$: C, 52.8; H, 3.0; N, 11.5. Found: C, 52.5; H, 3.0; N, 11.5.

Concentration of the recrystallization mother liquor gave 240 mg. of product, m.p. 226°-227° C. dec.

EXAMPLE 2

Employing the procedure of Example 1 and starting with 1-carbamoyloxindole and the appropriate isocyanate, the following compounds are prepared: 1-carbamoyloxindole-3-N-(3-furylmethyl)carboxamide; 1-carbamoyloxindole-3-N-(2-thienylmethyl)carboxamide; 1-carbamoyloxindole-3-N-(2,5-difluorophenyl)carboxamide; 1-carbamoyloxindole-3-N-(4-bromophenyl)carboxamide; 1-carbamoyloxindole-3-N-(3-chlorophenyl)carboxamide; 1-carbamoyloxindole-3-N-(4-fluorophenyl)carboxamide; 1-carbamoyloxindole-3-N-(4-i-propylphenyl)carboxamide; 1-carbamoyloxindole-3-N-(4-methylthiophenyl)carboxamide; 1-carbamoyloxindole-3-N-(3-trifluoromethylphenyl)carboxamide; 1-carbamoyloxindole-3-N-(4-acetylphenyl)carboxamide; 1-carbamoyloxindole-3-N-(4-n-butoxyphenyl)carboxamide; 1-carbamoyloxindole-3-N-(4-cyclohexylphenyl)carboxamide; 1-carbamoyloxindole-3-N-(2-fluoro-5-methylphenyl)carboxamide; 1-carbamoyloxindole-3-N-(2,4-dimethoxyphenyl)carboxamide; 1-carbamoyloxindole-3-N-(2,3-dimethylphenyl)carboxamide; 1-carbamoyloxindole-3-N-(2-ethoxy-4-methylthiophenyl)carboxamide; 1-carbamoyl-3-N-(3-trifluoromethyl-5-fluorophenyl)carboxamide; 1-carbamoyloxindole-3-N-(2-fluoro-4-acetylphenyl)carboxamide; 1-carbamoyloxindole-3-N-(3,5-dimethylthiophenyl)carboxamide; 1-carbamoyloxindole-3-N-(2-methyl-4-cyclopentylphenyl)carboxamide; and 1-carbamoyloxindole-3-N-(2-chloro-4-cyclohexylphenyl)carboxamide.

EXAMPLE 3

1-Carbamoyloxindole-3-N-(2-thienyl)carboxamide

Following the procedure of Example 1, a solution of 1.0 g. (0.0057 mole) of 1-carbamoyloxindole and 1.9 ml. (0.0136 mole) of triethylamine in 20 ml. of dimethylformamide was treated with 850 mg. (0.0068 mole) of 2-thienylisocyanate, and the reaction mixture allowed to stir for three hours at 5° C. The reaction mixture was added to 300 ml. of 1N hydrochloric acid and the resulting solid filtered, dried and recrystallized from acetonitrile, m.p. 210° C. dec. A small sample was further recrystallized from dimethylsulfoxide-water.

Anal. Calcd. for $C_{14}H_{11}O_3N_3S$: C, 55.8; H, 3.7; N, 14.0. Found: C, 55.8; H, 3.7; N, 14.0.

EXAMPLE 4

Starting with 1-carbamoyloxindole and the appropriate isocyanate and employing the procedure of Example 1 the following products are prepared:

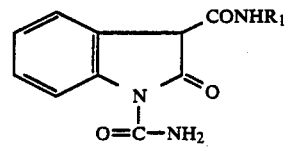

| $R_1$ |
| --- |
| 3-pyridyl |
| 6-methyl-2-pyridyl |
| 2-thienyl |
| 3-thienyl |
| 2-thiazolyl |
| 5-methyl-2-thiazolyl |
| 2-furyl |
| 2-oxazolyl |
| 3-isoxazolyl |
| 2-pyrrolyl |

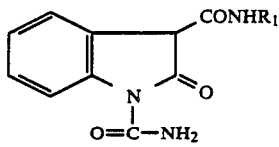

| R₁ |
|---|
| 2-pyridyl |
| 2-imidazolyl |
| 3-furyl |
| 5-methyl-3-isoxazolyl |

EXAMPLE 5

1-Carbamoyl-5-chlorooxindole-3-N-(i-propyl)carboxamide)

To a solution containing 1.0 g. (0.00475 mole) of 1-carbamoyl-5-chlorooxindole and 1.5 ml. (0.0104 mole) of triethylamine in 15 ml. of dimethylformamide cooled to 5° C. was added 0.5 ml. (0.0052 mole) of i-propylisocyanate, and the resulting reaction mixture allowed to stir for 30 minutes. Water (120 ml.) was added to the reaction mixture followed by 20 ml. of 1N hydrochloric acid, and the mixture allowed to stir for 20 minutes. The product was filtered, washed with water and suspended in 100 ml. of 0.05N methanolic hydrogen chloride. The mixture was heated to boiling and sufficient acetonitrile added to just dissolve the solids. The solution was allowed to cool overnight at room temperature. The product was filtered and recrystallized from acetonitrile, 350 mg., m.p. 223° C. dec.

Anal. Calcd. for $C_{13}H_{14}O_3N_3Cl$: C, 52.8; H, 4.8; N, 14.2. Found: C, 52.5; H, 4.8; N, 14.0.

EXAMPLE 6

Employing the procedure of Example 5 and starting with the appropriate 1-carbamoyloxindole and isocyanate, the following compounds are prepared:

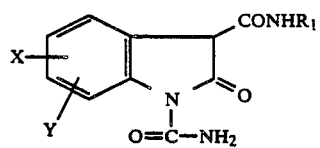

| X | Y | R₁ |
|---|---|---|
| 4-Cl | H | —CH₃ |
| 4-F | H | —CH(CH₃)₂ |
| H | H | —(CH₂)₃CH₃ |
| 5-Br | H | —(CH₂)₅CH₃ |
| 5-Cl | H | —(CH₂)₂CH₃ |
| 5-F | H | —(CH₂)₂CH(CH₃)₂ |
| H | 6-F | —CH₃ |
| H | 6-Br | —(CH₂)₅CH₃ |
| H | 6-Cl | —CH(CH₃)₂ |
| H | H | —(CH₂)₅CH₃ |
| H | 7-F | —(CH₂)₂CH(CH₃)₂ |
| H | 7-Cl | —(CH₂)₂CH₃ |
| 4-F | H |  |
| 4-Cl | H |  |

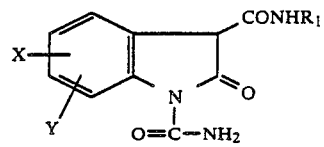

| X | Y | R₁ |
|---|---|---|
| 5-Cl | H |  |
| 5-Cl | H | (cyclohexyl) |
| H | 6-F | (cyclopropyl) |
| H | 7-F | (cycloheptyl) |
| H | 6-Cl | (cyclohexyl) |
| H | H | (cyclohexyl) |
| H | H | (cycloheptyl) |

EXAMPLE 7

1-Carbamoyl-5-chlorooxindole-3-N-(2,4-dichlorophenyl)carboxamide

To a cold (5° C.) solution of 1.0 g. (0.0047 mole) of 1-carbamoyl-5-chlorooxindole and 1.05 g. (0.0104 mole) of triethylamine in 20 ml. of dimethylformamide was added 980 mg. (0.0052 mole) of 2,4-dichlorophenylisocyanate, and the resulting reaction mixture allowed to stir for 30 minutes. Water (100 ml.) was added to the reaction mixture and the resulting triethylamine salt of the product filtered, washed with water and added to 100 ml. 0.05N methanolic hydrogen chloride. The solids were filtered, washed with hot methanol and dried, 1.0 g., m.p. 282° C. dec.

Anal. Calcd. for $C_{16}H_{10}O_3N_3Cl_3$: C, 48.2; H, 2.5; N, 10.5. Found: C, 48.2; H, 2.7; N, 10.4.

EXAMPLE 8

Following the procedure of Example 7, and starting with 1-carbamoyl-5-chlorooxindole and the appropriate isocyanate, the indicated products were prepared:

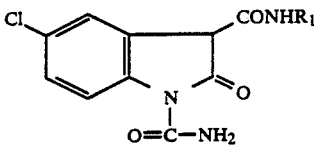

| $R_1$ | m.p., °C., dec. | Anal. |
|---|---|---|
| 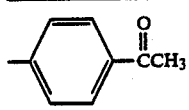 —CCH₃ (with C=O) | 217 | For C₁₈H₁₄O₄N₃Cl— Calcd.:C,58.2;H,3.8; N,11.3. Found:C,58.0;H,3.8; N,11.2. |
| 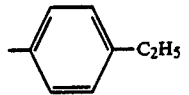 —C₂H₅ | 229 | For C₁₈H₁₆O₃N₃Cl— Calcd.:C,60.4;H,4.5; N,11.7. Found:C,60.2;H,4.6; N,11.7. |
| 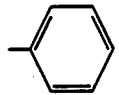 | 228 | For C₁₆H₁₂O₃N₃Cl— Calcd.:C,58.3;H,3.7; N,12.7. Found:C,58.0;H,3.8; N,12.8. |
| 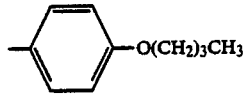 —O(CH₂)₃CH₃ | 223 | For C₂₀H₂₀O₄N₃Cl— Calcd.:C,59.8;H,5.0; N,10.5. Found:C,59.4;H,4.9; N,10.5. |
| 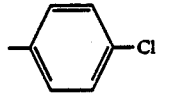 —Cl | 230 | For C₁₆H₁₁O₃N₃Cl₂— Calcd.:C,52.8;H,3.0; N,11.5. Found:C,52.8;H,3.0; N,11.6. |
| 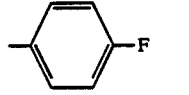 —F | 227–229 | For C₁₆H₁₁O₃N₃ClF— Calcd.:C,55.3;H,3.2; N,12.1. Found:C,55.0;H,3.4; N,12.1. |
| 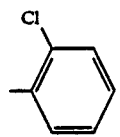 (Cl ortho) | 220–221.5 | For C₁₆H₁₁O₃N₃Cl₂— Calcd.:C,52.8;H,3.0; N,11.5. Found:C,52.9;H,3.1; N,11.8. |
| 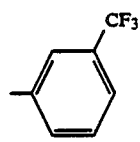 CF₃ | 203–204 | For C₁₇H₁₁O₃N₃ClF₃— Calcd.:C,51.1;H,2.9; N,10.6. Found:C,51.1;H,2.9; N,10.5. |
| 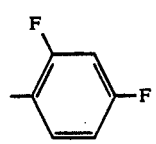 F,F | 219 | For C₁₆H₁₀O₃N₃ClF₂— Calcd.:C,52.6;H,2.8; N,11.5. Found:C,52.5;H,2.8; N,11.6. |

EXAMPLE 9

Starting with the requisite isocyanate and 1-carbamoyloxindole, and employing the procedure of Example 7, the following products are prepared: 1-carbamoyl-4-fluoroxindole-3-N-(4-methylthiophenyl)carboxamide; 1-carbamoyl-4-fluorooxindole-3-N-(4-propionylphenyl)carboxamide; 1-carbamoyl-4-chlorooxindole-3-N(3-methoxyphenyl)carboxamide; 1-carbamoyl-4-chlorooxindole-3-N-(2-methyl-5-methoxyphenyl)carboxamide; 1-carbamoyl-4-bromooxindole-3-N(4-cyclohexylphenyl)carboxamide; 1-carbamoyl-4-bromooxindole-3-N-(3-methyl-5-trifluoromethylphenyl)carboxamide; 1-carbamoyl-5-fluorooxindole-3-N-(4-propionylphenyl)carboxamide; 1-carbamoyl-5-fluorooxindole-3-N-(4-ethylphenyl)carboxamide; 1-carbamoyl-5-fluorooxindole-3-N-(2-chloro-4-fluorophenyl)carboxamide; 1-carbamoyl-5-chlorooxindole-3-N-(3-trifluoromethyl-5-chlorophenyl)carboxamide; 1-carbamoyl-5-chlorooxindole-3-N-(3-methoxy-4-n-propylthiophenyl)carboxamide; 1-carbamoyl-5-chlorooxindole-3-N-(2-fluoro-4-acetylphenyl)carboxamide; 1-carbamoyl-5-bromooxindole-3-N-(2-chloro-4-cyclopentylphenyl)carboxamide; 1-carbamoyl-5-bromooxindole-3-N-(2-fluoro-4-bromophenyl)carboxamide; 1-carbamoyl-6-fluorooxindole-3-N-(4-tolyl)carboxamide; 1-carbamoyl-6-fluorooxindole-3-N-(phenyl)carboxamide; 1-carbamoyl-6-fluorooxindole-3-N-(4-butoxyphenyl)carboxamide; 1-carbamoyl-6-chlorooxindole-3-N-(2-chloro-4-acetylphenyl)carboxamide; 1-carbamoyl-6-bromooxindole-3-N-(2,4-difluorophenyl)carboxamide; 1-carbamoyl-6-bromooxindole-3-N-(4-cyclohexylphenyl)carboxamide; 1-carbamoyl-7-fluorooxindole-3-N-(3-methoxy-4-n-propylthiophenyl)carboxamide; 1-carbamoyl-7-chlorooxindole-3-N-(4-bromophenyl)carboxamide; 1-carbamoyl-7-chlorooxindole-3-N-(2-fluoro-4-cyclohexylphenyl)carboxamide; and 1-carbamoyl-7-bromooxindole-3-N-(2-chloro-4-ethylthiophenyl)carboxamide.

EXAMPLE 10

1-Carbamoyl-5-chlorooxindole-3-N-(2-thienyl)carboxamide

To a cold (5° C.) solution of 20 ml. of dimethylformamide containing 1 g. (0.00475 mole) of 1-carbamoyl-5-chlorooxindole and 2 ml. (0.014 mole) of triethylamine was added 10 ml. of 2-thienylisocyanate, and the reaction mixture allowed to stir for 1 hour. Ethyl acetate (50 ml.) and 200 ml. of 1N hydrochloric acid were added and the solids were filtered and recrystallized from ethyl acetate, 200 mg., m.p. 199° C., dec.

Anal. Calcd. for C₁₄H₁₀O₃N₃ClS: C, 50.1; H, 3.0; N, 12.5. Found: C, 50.0; H, 2.9; N, 12.3.

EXAMPLE 11

Starting with the appropriate 1-carbamoylhalooxinde and isocyanate and employing the procedure of Example 10, the following compounds are prepared:

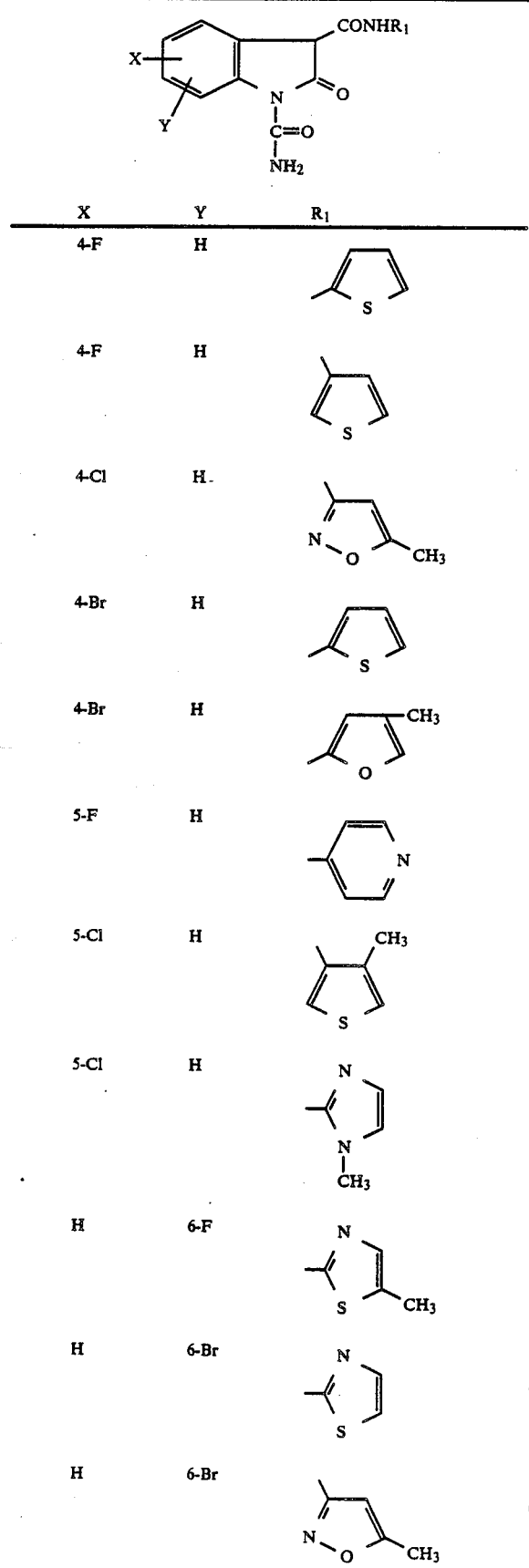

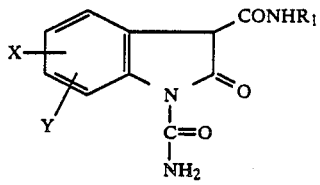

| X | Y | R₁ |
|---|---|---|
| H | 7-F | 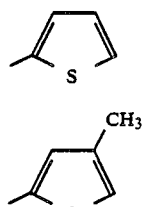 |
| H | 7-F | ![](CH₃ on furan) |

EXAMPLE 12

1-Carbamoyl-6-trifluoromethyloxindole-3-N-(4-chlorophenyl)carboxamide

To a solution of 350 mg. (0.0014 mole) of 1-carbamoyl-6-trifluoromethyloxindole and 0.24 ml. (0.0034 mole) of triethylamine in 5 ml. of dimethylformamide cooled to 5° C. was added 261 mg. (0.0017 mole) of 4-chlorophenylisocyanate, and the reaction mixture stirred for 1.5 hours. The mixture was added to 100 ml. of 1N hydrochloric acid and allowed to stir for 30 minutes. The solids were filtered, washed with water and crystallized from acetonitrile, 340 mg., m.p. 216° C., dec.

Anal. Calcd. for $C_{17}H_{11}O_3N_3ClF_3$: C, 51.3; H, 2.8; N, 10.6. Found: C, 51.1; H, 2.9; N, 10.6.

EXAMPLE 13

1-Carbamoyl-6-trifluoromethyloxindole-3-N-(2,4-dichlorophenyl)carboxamide

In a manner similar to Example 12, 350 mg. (0.0014 mole) of 1-carbamoyl-6-trifluoromethyloxindole and 0.24 ml. (0.0034 mole) of triethylamine were added to 5 ml. of dimethylformamide at 5° C. followed by 320 mg. (0.0017 mole) of 2,4-dichlorophenylisocyanate. The resulting reaction mixture was allowed to stir for 2 hours and was then poured into 100 ml. of 1N hydrochloric acid. The resulting solid suspension was allowed to stir for 30 minutes and was then filtered. The solids were washed with acid and water and air dried for one hour. Crystallization from acetonitrile gave 200 mg. of the desired product. 214° C. dec.

Anal. Calcd. for $C_{17}H_{10}O_3N_3Cl_2F_3 \cdot \frac{1}{2}CH_3CN$: C, 47.8; H, 2.6; N, 10.8. Found: C, 47.4; H, 2.6; N, 10.9.

EXAMPLE 14

Employing the procedure of Examples 12/13 and starting with the appropriate isocyanate and 1-carbamoyloxindole, the following compounds are prepared:

1-carbamoyl-4-trifluoromethyloxindole-3-N-(phenyl)carboxamide; 1-carbamoyl-4-trifluoromethyloxindole-3-N-(i-propyl)carboxamide; 1-carbamoyl-4-trifluoromethyloxindole-3-N-(4-methoxyphenyl)carboxamide; 1-carbamoyl-4-trifluoromethyloxindole-3-N-(cyclohexyl)carboxamide; 4-trifluoromethyloxindole-3-

N-(2-chloro-4-methylphenyl)carboxamide; 1-carbamoyl-5-trifluoromethyloxindole-3-N-(3,4-dimethoxyphenyl)carboxamide; 1-carbamoyl-5-trifluoromethyloxindole-3-N-(3-trifluoromethylphenyl)carboxamide; 1-carbamoyl-5-trifluoromethyloxindole-3-N-(4-propionylphenyl)carboxamide; 1-carbamoyl-5-trifluoromethyloxindole-3-N-(2-fluoro-4-methylthiophenyl)carboxamide; 1-carbamoyl-5-trifluoromethyloxindole-3-N-(4-butoxyphenyl)carboxamide; 1-carbamoyl-5-trifluoromethyloxindole-3-N-(2-chloro-4-acetylphenyl)carboxamide; 1-carbamoyl-5-trifluoromethyloxindole-3-N-(phenyl)carboxamide; 1-carbamoyl-6-trifluoromethyloxindole-3-N-(2-methoxy-4-ethylphenyl)carboxamide; 1-carbamoyl-6-trifluoromethyloxindole-3-N-(cycloheptyl)carboxamide; 1-carbamoyl-6-trifluoromethyloxindole-3-N-(t-butyl)carboxamide; 1-carbamoyl-6-trifluoromethyloxindole-3-N-(2,4-difluorophenyl)carboxamide; 1-carbamoyl-6-trifluoromethyl-oxindole-3-N-(2-fluoro-3-chlorophenyl)carboxamide; 1-carbamoyl-7-trifluoromethyloxindole-3-N-(3,4-dimethylthiophenyl)carboxamide; 1-carbamoyl-7-trifluoromethyloxindole-3-N-(3-trifluoromethyl-5-chlorophenyl)carboxamide; and 1-carbamoyl-7-trifluoromethyloxindole-3-N-(phenyl)carboxamide.

EXAMPLE 15

Starting with the requisite reagents and employing the procedure of Example 12, the following compounds are prepared:

| X | Y | R$_1$ |
|---|---|---|
| 4-CF$_3$ | H | (2-thienyl) |
| 4-CF$_3$ | H | (3-methyl-5-methylfuranyl) |
| 4-CF$_3$ | H | (2-methyl-5-methylthiazolyl) |
| 4-CF$_3$ | H | (3-methyl-5-methylisoxazolyl) |
| 4-CF$_3$ | H | (N-methylpyrazinyl) |
| 5-CF$_3$ | H | (3-methyl-5-methylisoxazolyl) |
| 5-CF$_3$ | H | (2-methyl-5-methylthiazolyl) |
| 5-CF$_3$ | H | (4-methylthienyl) |
| H | 6-CF$_3$ | (4-methylthienyl) |
| H | 6-CF$_3$ | (2-methylthienyl) |
| H | 6-CF$_3$ | (N-methyl-2-methylpyrrolyl) |
| H | 6-CF$_3$ | (4-methyl-2-methylthienyl) |
| H | 7-CF$_3$ | (2-methylpyridyl) |
| H | 7-CF$_3$ | (3-methyl-4-methylfuranyl) |
| H | 7-CF$_3$ | (4-methyl-2-methylthienyl) |

EXAMPLE 16

1-Carbamoyl-5-acetyloxindole-3-N-(phenyl)carboxamide

Phenylisocyanate (0.6 ml., 0.0055 mole) was added to a solution of 1.0 g. (0.0045 mole) of 1-carbamoyl-5-acetyloxindole and 1.5 ml. (0.011 mole) of triethylamine in 35 ml. of dimethylformamide cooled to 0°–5° C., and the mixture allowed to stir for 2 hours. The mixture was added to 300 ml. of 1N hydrochloric acid and allowed to stir for 30 minutes. The product was filtered, washed with water and air dried. Crystallization from acetonitrile gave 800 mg. of product, m.p. 213° C., dec.

Anal. Calcd. for $C_{18}H_{15}O_4N_3$: C, 64.1; H, 4.5; N, 12.4. Found: C, 63.8; H, 4.4; N, 12.4.

EXAMPLE 17

1-Carbamoyl-5-acetyloxindole-3-N-(4-chlorophenyl)-carboxamide

In a manner similar to Example 16, 1.0 g. (0.00458 mole) of 1-carbamoyl-5-acetyloxindole, 1.5 ml. of triethylamine and 845 mg. (0.0055 mole) of 4-chlorophenylisocyanate in 35 ml. of dimethylformamide gave on work-up and crystallization from dimethylformamide-water 1.0 g. of product, m.p. 212° C., dec.

Anal. Calcd. for $C_{18}H_{14}O_4N_3Cl$: C, 58.2; H, 3.8; N, 11.3. Found: C, 57.8; H, 3.7; N, 11.1.

EXAMPLE 18

Employing the procedure of Example 16 and starting with the appropriate isocyanate and 1-carbamoyloxindole, the following compounds are prepared:

1-carbamoyl-4-acetyloxindole-3-N-(phenyl)carboxamide; 1-carbamoyl-4-acetyloxindole-3-N-(i-propyl)carboxamide; 1-carbamoyl-4-acetyloxindole-3-N-(4-methoxyphenyl)carboxamide; 1-carbamoyl-4-acetyloxindole-3-N-(cyclohexyl)carboxamide; 1-carbamoyl-4-acetyloxindole-3-N-(3,4-dimethoxyphenyl)carboxamide; 1-carbamoyl-4-acetyloxindole-3-N-(2-chloro-4-methyl-phenyl)carboxamide; 1-carbamoyl-5-propionyloxindole-3-N-(4-propionylphenyl)carboxamide; 1-carbamoyl-5-propionyloxindole-3-N-(3-trifluoromethylphenyl)carboxamide; 1-carbamoyl-5-propionyloxindole-3-N-(4-butoxyphenyl)carboxamide; 1-carbamoyl-5-propionyloxindole-3-N-(2-fluoro-4-methylphenyl)carboxamide; 1-carbamoyl-6-butyryloxindole-3-N-(phenyl)carboxamide; 1-carbamoyl-6-butyryloxindole-3-carboxamide; 1-carbamoyl-6-butyryloxindole-3-N-(2-methoxy-4-ethylphenyl)carboxamide; 1-carbamoyl-7-acetyloxindole-3-N-(cycloheptyl)carboxamide; 1-carbamoyl-7-acetyloxindole-3-N-(t-butyl)-carboxamide; 1-carbamoyl-7-acetyloxindole-3-N-(2,4-difluorophenyl)carboxamide; 1-carbamoyl-7-acetyloxindole-3-N-(2-fluoro-3-chlorophenylcarboxamide; 1-carbamoyl-7-propionyloxindole-3-N-(3,4-dimethylthiophenyl)carboxamide; 1-carbamoyl-7-propionyloxindole-3-N-(3-trifluoromethyl-5-chlorophenyl)carboxamide; 1-carbamoyl-7-propionyloxindole-3-N-(phenyl)carboxamide and 1-carbamoyl-7-propionyloxindole-3-N-(2,4-difluorophenyl)carboxamide.

EXAMPLE 19

Starting with the requisite 1-carbamoyloxindole and isocyanate and using the procedure of Example 16, the following compounds are prepared:

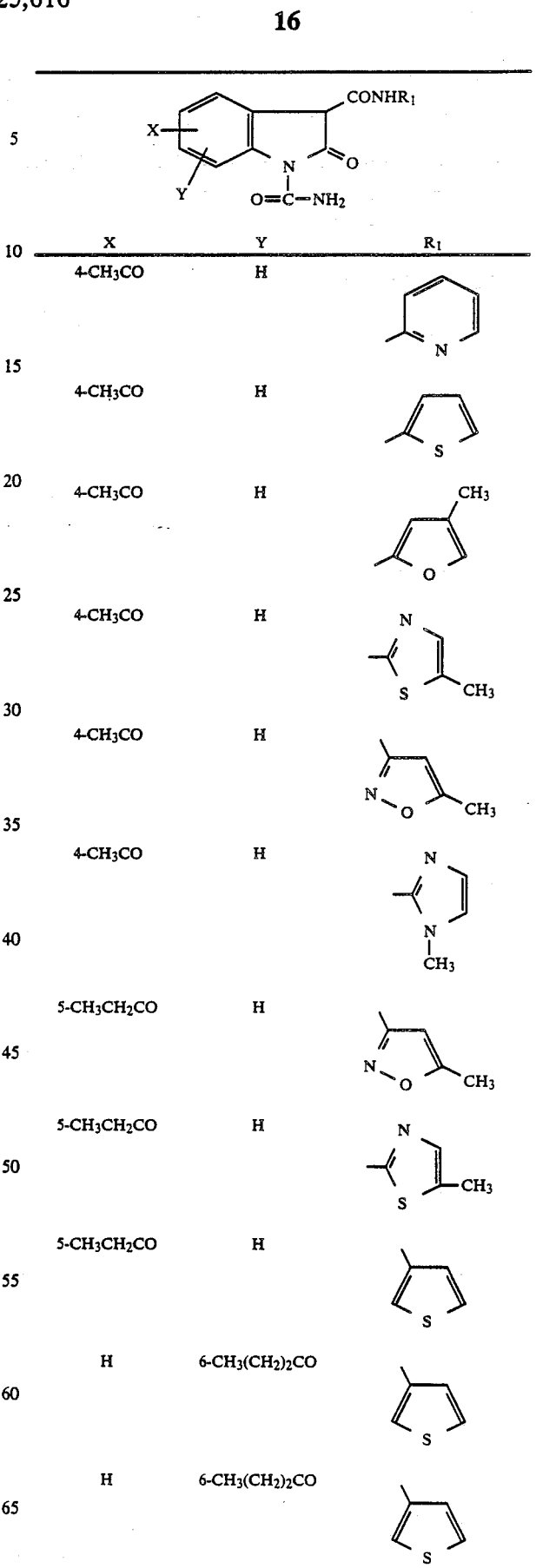

-continued

| X | Y | R$_1$ |
|---|---|---|
| H | 6-CH$_3$(CH$_2$)$_2$CO | (N-methylpyrrolyl) |
| H | 6-CH$_3$(CH$_2$)$_2$CO | (methylthienyl-CH$_3$) |
| H | 7-CH$_3$CO | (methylfuranyl-CH$_3$) |
| H | 7-CH$_3$CO | (methylthienyl-CH$_3$) |
| H | 7-CH$_3$CH$_2$CO | (methylisoxazolyl-CH$_3$) |

EXAMPLE 20

1-Carbamoyl-5-benzoyloxindole-3-N-(phenyl)carboxamide

To 1.0 g. (0.00357 mole) of 1-carbamoyl-5-benzoyloxindole and 1.2 ml. (0.00856 mole) of triethylamine in 25 ml. of dimethylformamide cooled to 5° C. was added 0.465 ml. (0.00428 mole) of phenylisocyanate, and the reaction mixture stirred for 2 hours. The mixture was then poured into 250 ml. of 1N hydrochloric acid and the mixture stirred for 30 minutes. The solids were filtered washed with acid and water and air dried. Crystallization from methanol-acetonitrile gave 800 mg. of the desired product, m.p. 214° C., dec.

Anal. Calcd. for C$_{23}$H$_{17}$O$_4$N$_3$: C, 69.2; H, 4.3; N, 10.5. Found: C, 69.1; H, 4.4; N, 10.5.

EXAMPLE 21

1-Carbamoyl-5-benzoyloxindole-3-N-(4-chlorophenyl)-carboxamide

In a manner similar to Example 20, 1.0 g. (0.00357 mole) of 1-carbamoyl-5-benzoyloxindole, 657 mg. (0.00428 mole) of 4-chlorophenylisocyanate and 1.2 ml. (0.00856 mole) of triethylamine in 25 ml. of dimethylformamide gave on work-up 550 mg. of product after crystallization from methanol-acetonitrile m.p. 219° C., dec.

Anal. Calcd. for C$_{23}$H$_{16}$O$_4$N$_3$Cl: C, 63.7; H, 3.7; N, 9.7. Found: C, 63.5; H, 3.8; N, 9.7.

EXAMPLE 22

Employing the procedure of Example 20 and starting with the appropriate 1-carbamoyloxindole and isocyanate, the following compounds are prepared:

1-carbamoyl-4-benzoyloxindole-3-N-(2,4-difluorophenyl)carboxamide; 1-carbamoyl-4-benzoyloxindole-3-N-(phenyl)carboxamide; 1-carbamoyl-4-benzoyloxindole-3-N-(3-trifluoromethyl-5-chlorophenyl)carboxamide; 1-carbamoyl-4-benzoyloxindole-3-N(3,4-dimethylthiophenyl)carboxamide; 1-carbamoyl-4-benzoyloxindole-3-N-(2-fluoro-3-chlorophenyl)carboxamide; 1-carbamoyl-5-benzoyloxindole-3-N-(2,4-difluorophenyl)carboxamide; 1-carbamoyl-5-benzoyloxindole-3-N-(t-butyl)carboxamide; 1-carbamoyl-5-benzoyloxindole-3-N-(cycloheptyl)carboxamide; 1-carbamoyl-5-benzoyloxindole-3-N-(2-methoxy-4-ethylphenyl)carboxamide; 1-carbamoyl-5-benzoyloxindole-3-N-(phenyl)carboxamide; 1-carbamoyl-6-benzoyloxindole-3-N-(2-fluoro-4-methylphenyl)carboxamide; 1-carbamoyl-6-benzoyloxindole-3-N-(4-butoxyphenyl)carboxamide; 1-carbamoyl-6-benzoyloxindole-3-N-(i-propyl)carboxamide; 1-carbamoyl-6-benzoyloxindole-3-N-(4-methoxyphenyl)carboxamide; 1-carbamoyl-6-benzoyloxindole-3-N-(cyclohexyl)carboxamide; 1-carbamoyl-7-benzoyloxindole-3-N-(3,4-dimethoxyphenyl)carboxamide; 1-carbamoyl-7-benzoyloxindole-3-N-(2-chloro-4-methylphenyl)carboxamide; 1-carbamoyl-7-benzoyloxindole-3-N-(4-propionylphenyl)carboxamide; and 1-carbamoyl-7-benzoyloxindole-3-N-(3-trifluoromethylphenyl)carboxamide.

EXAMPLE 23

Starting with the requisite 1-carbamoyloxindole and isocyanate and using the procedure of Example 20, the following compounds are prepared.

| X | Y | R$_1$ |
|---|---|---|
| 4-(phenyl)CO | H | (N-methylimidazolyl) |
| 4-(phenyl)CO | H | (methylisoxazolyl-CH$_3$) |
| 4-(phenyl)CO | H | (methylthienyl-CH$_3$) |
| 4-(phenyl)CO | H | (methylfuranyl-CH$_3$) |

-continued

Structure: oxindole with X, Y substituents, 3-CONHR₁, and N-C(=O)-NH₂ (1-carbamoyl)

| X | Y | R₁ |
|---|---|---|
| 4-(phenyl-CO) | H | 2-thienyl (methyl) |
| 5-(phenyl-CO) | H | 3-methyl-isoxazol-5-yl (CH₃) |
| 5-(phenyl-CO) | H | 2-methyl-thiazol-4-yl (CH₃) |
| 5-(phenyl-CO) | H | 3-thienyl |
| H | 6-(phenyl-CO) | 3-thienyl |
| H | 6-(phenyl-CO) | 2-thienyl |
| H | 6-(phenyl-CO) | 1-methyl-pyrrol-2-yl |
| H | 6-(phenyl-CO) | 1-methyl-imidazol-2-yl |
| H | 7-(phenyl-CO) | 3-pyridyl |
| H | 7-(phenyl-CO) | 4-methyl-furan-2-yl (CH₃) |
| H | 7-(phenyl-CO) | 4-methyl-thien-2-yl (CH₃) |
| H | 7-(phenyl-CO) | 3-methyl-isoxazol-5-yl (CH₃) |

EXAMPLE 24

1-Carbamoyl-5-(2-thenoyl)oxindole-3-N-(phenyl)carboxamide

To 1.0 g. (0.0035 mole) of 1-carbamoyl-5-(2-thenoyl)oxindole in 25 ml. of dimethylformamide at 0°–5° C. was added 1.2 ml. (0.0084 mole) of triethylamine followed by 0.456 ml. (0.0042 mole) of phenylisocyanate. After stirring for 2 hours, the reaction mixture was added to 300 ml. of 1N hydrochloric acid and allowed to stir for 30 minutes. The filtered solids were washed with water and air dried. Crystallization from acetonitrile gave 700 mg. of the desired product, m.p. 222° C., dec.

Anal. Calcd. for $C_{21}H_{15}O_4N_3S$: C, 62.2; H, 3.7; N, 10.4. Found: C, 62.2; H, 3.8; N, 10.1.

EXAMPLE 25

1-Carbamoyl-5-(2-thenoyl)oxindole-3-N-(4-chlorophenyl)carboxamide

In a manner similar to Example 24, 1.0 g. (0.0035 mole) of 1-carbamoyl-5-(2-thenoyl)oxindole, 640 mg. of 4-chlorophenylisocyanate and 1.2 ml. (0.0084 mole) of triethylamine in 25 ml. of dimethylformamide gave on work-up 1.2 g. of product after crystallization from acetonitrile, m.p. 223° C., dec.

Anal. Calcd. for $C_{21}H_{14}O_4N_3ClS$: C, 57.3; H, 3.2; N, 9.6. Found: C, 57.5; H, 3.3; N, 9.9.

EXAMPLE 26

Starting with the appropriate 1-carbamoyloxindole and isocyanate and employing the procedures of Example 24, the following compounds are proposed:
1-carbamoyl-4-(2-thenoyl)oxindole-3-N-(2,4-difluorophenyl)carboxamide; 1-carbamoyl-4-(2-thenoyl)oxindole-3-N-(t-butyl)carboxamide; 1-carbamoyl-4-(3-thenoyl)oxindole-3-N-(cycloheptyl)carboxamide; 1-carbamoyl-4-(3-thenoyl)oxindole-3-N-(2-methoxy-4-ethylphenyl)carboxamide; 1-carbamoyl-4-(3-thenoyl)oxindole-3-N-(phenyl)carboxamide; 1-carbamoyl-5-(2-thenoyl)oxindole-3-N-(2-chloro-4-acetylphenyl)carboxamide; 1-carbamoyl-5-(2-thenoyl)oxindole-3-N-(4-butoxyphenyl)carboxamide; 1-carbamoyl-5-(3-thenoyl)oxindole-3-N-(2-fluoro-4-methylphenyl)carboxamide; 1-carbamoyl-5-(2-thenoyl)oxindole-3-N-(4-propionylphenyl)carboxamide; 1-carbamoyl-5-(3-thenoyl)oxindole-3-N-(3-trifluoromethylphenyl)carboxamide; 1-carbamoyl-6-(2-thenoyl)oxindole-3-N-(3,4-dimethoxyphenyl)carboxamide; 1-carbamoyl-6-(2-thenoyl)oxindole-3-N-(cyclohexyl)carboxamide; 1-carbamoyl-6-(3-thenoyl)oxindole-3-N-(4-methoxyphenyl)carboxamide; 1-carbamoyl-6-(3-thenoyl)oxindole-3-N-

(i-propyl)carboxamide; 1-carbamoyl-7-(2-thenoyl)oxindole-3-N-(phenyl)carboxamide; 1-carbamoyl-7-(2-thenoyl)oxindole-3-N-(2-fluoro-3-chlorophenyl)carboxamide; 1-carbamoyl-7-(3-thenoyl)oxindole-3-N-(3,4-dimethylthiophenyl)carboxamide; 1-carbamoyl-7-(3-thenoyl)oxindole-3-N-(3-trifluoromethyl-5-chlorophenyl)carboxamide; and 1-carbamoyl-7-(3-thenoyl)oxindole-3-N-(phenyl)carboxamide.

EXAMPLE 27

Employing the procedure of Example 24 and starting with the requisite 1-carbamoyloxindole and isocyanate, the following compounds are prepared:

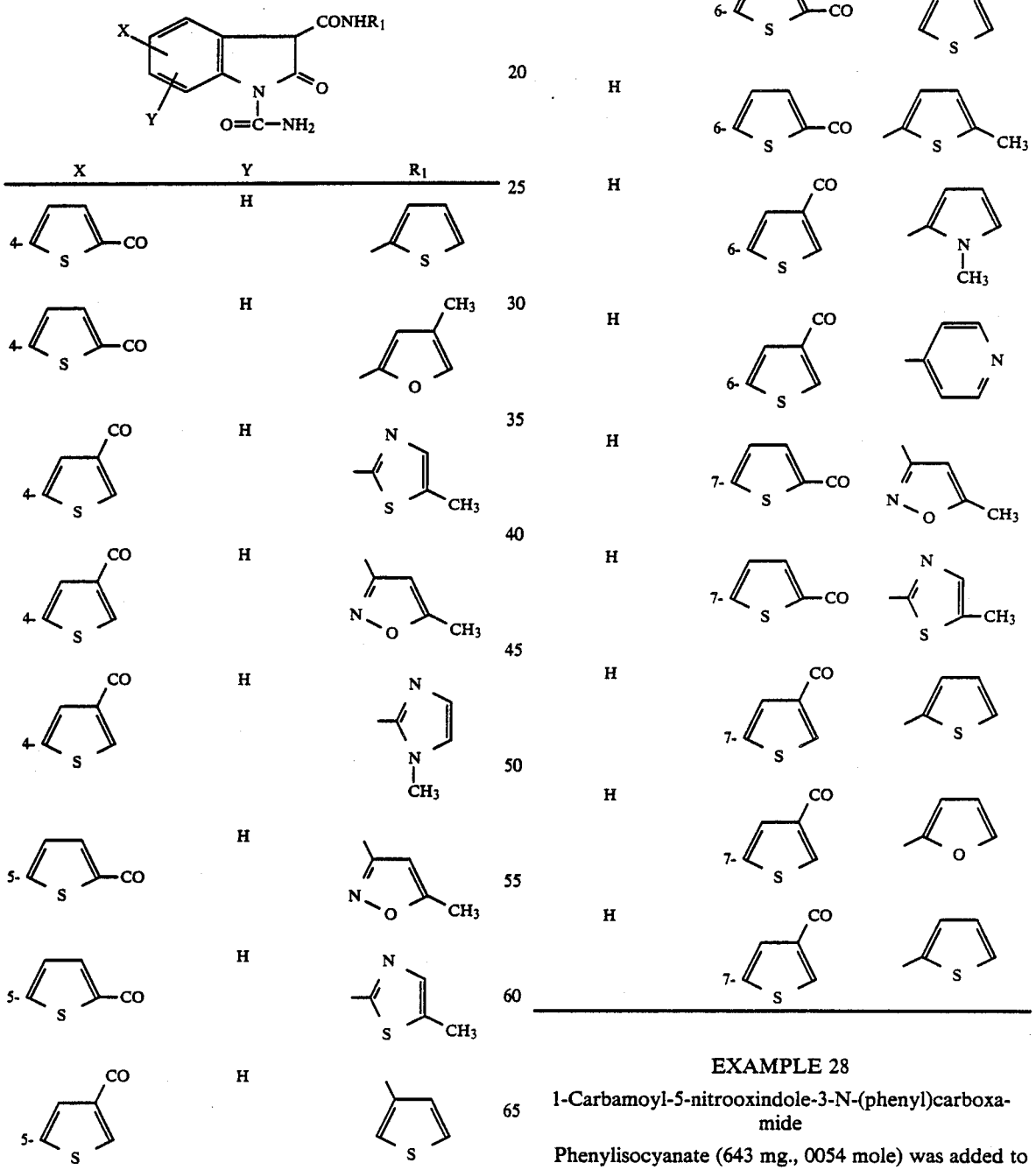

EXAMPLE 28

1-Carbamoyl-5-nitrooxindole-3-N-(phenyl)carboxamide

Phenylisocyanate (643 mg., 0054 mole) was added to a solution of 1.0 g. (0.0045 mole) of 1-carbamoyl-5- nitrooxindole and 1.09 g. (0.0011 mole) of triethylamine in 25 ml. of dimethylformamide at 0° C. and the resulting reaction mixture allowed to stir for 2 hours. The mixture was poured into 300 ml. of 1N hydrochloric acid and stirred for 30 minutes. The solids were filtered, washed with acid and water and crystallized from propanol-acetonitrile to give 340 mg. of the desired product, m.p. 219° C., dec.

Anal. Calcd. for $C_{16}H_{12}O_5N_4$: C, 56.5; H, 3.6; N, 16.5. Found: C, 56.5; H, 3.7; N, 16.2.

In a similar manner 1-carbamoyl-5-nitrooxindole-3-N-(4-chlorophenyl)carboxamide was prepared, m.p. 215° C., dec.

Anal. Calcd. for $C_{16}H_{11}O_5N_4Cl$: C, 51.3; H, 3.0; N, 15.0. Found: C, 51.2; H, 3.0; N, 14.9.

EXAMPLE 29

Using the procedure of Example 28 and starting with the appropriate isocyanate and 1-carbamoyloxindole, the following compounds are prepared:

1-carbamoyl-4-nitrooxindole-3-N-(2,4-difluorophenyl)carboxamide; 1-carbamoyl-4-nitrooxindole-3-N-(t-butyl)carboxamide; 1-carbamoyl-4-nitrooxindole-3-N-(i-propyl)carboxamide; 1-carbamoyl-4-nitrooxindole-3-N-(cyclohexyl)carboxamide; 1-carbamoyl-4-nitrooxindole-3-N-(2-methoxy-4-ethylphenyl)carboxamide; 1-carbamoyl-5-nitrooxindole-3-N-(2-chloro-4-acetylphenyl)carboxamide; 1-carbamoyl-5-nitrooxindole-3-N-(4-butoxyphenyl)carboxamide; 1-carbamoyl-5-nitrooxindole-3-N-(2-fluoro-4-methylphenyl)carboxamide; 1-carbamoyl-5-nitrooxindole-3-N-(4-propionylphenyl)carboxamide; 1-carbamoyl-5-nitrooxindole-3-N-(3-trifluoromethylphenyl)carboxamide; 1-carbamoyl-5-nitrooxindole-3-N-(3,4-dimethoxyphenyl)carboxamide; 1-carbamoyl-5-nitrooxindole-3-N-(cycloheptyl)carboxamide; 1-carbamoyl-6-nitrooxindole-3-N-(4-methoxyphenyl)carboxamide; 1-carbamoyl-6-nitrooxindole-3-N-(i-propyl)carboxamide; 1-carbamoyl-6-nitrooxindole-3-N-(phenyl)carboxamide; 1-carbamoyl-6-nitrooxindole-3-N-(2-fluoro-3-chlorophenyl)carboxamide; 1-carbamoyl-7-nitrooxindole-3-N-(3,4-dimethylthiophenyl)carboxamide; 1-carbamoyl-7-nitrooxindole-3-N-(3-trifluoromethyl-5-chlorophenyl)carboxamide; 1-carbamoyl-7-nitrooxindole-3-N-(cyclohexyl)carboxamide; and 1-carbamoyl-7-nitrooxindole-3-N-(2,5-difluorophenyl)-carboxamide.

EXAMPLE 30

Employing the procedure of Example 28 and starting with the requisite isocyanate and 1-carbamoyloxindole, the following compounds are prepared:

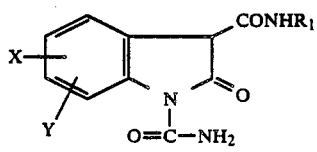

| X | Y | $R_1$ |
|---|---|---|
| 4-NO$_2$ | H | 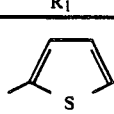 |
| 4-NO$_2$ | H | 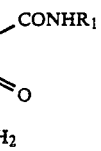 |
| 4-NO$_2$ | H | 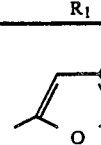 |
| 4-NO$_2$ | H | 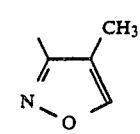 |
| 5-NO$_2$ | H | 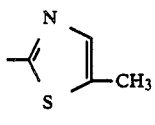 |
| 5-NO$_2$ | H | 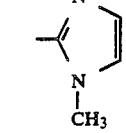 |
| 5-NO$_2$ | H | 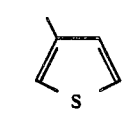 |
| H | 6-NO$_2$ | 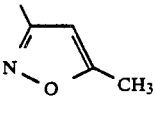 |
| H | 6-NO$_2$ | 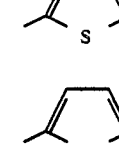 |
| H | 6-NO$_2$ | 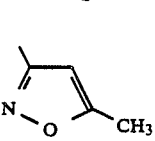 |
| H | 6-NO$_2$ | 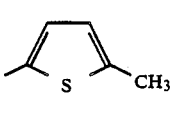 |
| H | 6-NO$_2$ | 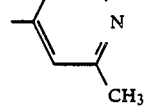 |

-continued

[Structure: oxindole with CONHR₁ at 3-position, X and Y substituents, N-C(=O)-NH₂ at N1]

| X | Y | R₁ |
|---|---|---|
| H | 7-NO₂ | [thiazole with CH₃] |
| H | 7-NO₂ | [N-methyl imidazole] |
| H | 7-NO₂ | [N-methyl pyrrole] |
| H | 7-NO₂ | [methylthiophene with CH₃] |
| H | 7-NO₂ | [dimethyl furan] |

EXAMPLE 31

1-Carbamoyl-5-methyloxindole-3-N-(phenyl)carboxamide

To a solution of 1.76 g. (0.01 mole) of 1-carbamoyl-5-methyloxindole and 2.4 g. (0.24 mole) of triethylamine in 20 ml. of dimethylformamide cooled to 0°–5° C. is added 1.43 g. (0.012 mole) of phenylisocyanate, and the mixture stirred for 2.5 hours. The mixture is added to 375 ml. of 1N hydrochloric acid and allowed to stir for 30 minutes. The solids are filtered, washed with water and crystallized from acetonitrile to give the desired product.

EXAMPLE 32

Using the procedure of Example 31 and starting with the appropriate reagents, the following compounds are prepared:
1-carbamoyl-4-methyloxindole-3-N-(2,5-difluorophenyl)carboxamide; 1-carbamoyl-4-methyloxindole-3-N-(t-butyl)carboxamide; 1-carbamoyl-4-ethyloxindole-3-N-(i-propyl)carboxamide; 1-carbamoyl-4-ethyloxindole-3-N-(phenyl)carboxamide; 1-carbamoyl-4-ethyloxindole-3-N-(cyclohexyl)carboxamide; 1-carbamoyl-5-methyloxindole-3-N-(2-methoxy-4-ethylphenyl)carboxamide; 1-carbamoyl-5-methyloxindole-3-N-(2-chloro-4-acetylphenyl)carboxamide; 1-carbamoyl-5-methyloxindole-3-N-(2-fluoro-4-methylphenyl)carboxamide; 1-carbamoyl-5-n-propyloxindole-3-carboxamide; 1-carbamoyl-5-n-propyloxindole-3-N-(3-trifluoromethylphenyl)carboxamide; 1-carbamoyl-5-n-propyloxindole-3-N-(cycloheptyl)carboxamide; 1-carbamoyl-5-n-butyloxindole-3-N-(4-methoxyphenyl)-carboxamide; 1-carbamoyl-5-n-butyloxindole-3N-(i-propyl)carboxamide; 1-carbamoyl-6-methyloxindole-3-N-(2-fluoro-3-chlorophenyl)carboxamide; 1-carbamoyl-6-methyloxindole-3-N-(2-fluoro-3-chlorophenyl)carboxamide; 1-carbamoyl-6-methyloxindole-3-N-(3,4-dimethoxyphenyl)carboxamide; 1-carbamoyl-6-methyloxindole-3-N-(3-trifluoromethyl-5-chlorophenyl)carboxamide; 1-carbamoyl-6-i-propyloxindole-3-N-(2,5-difluorophenyl)carboxamide; 1-carbamoyl-7-methyloxindole-3-N-(3,4-dimethylthiophenyl)carboxamide; 1-carbamoyl-7-methyloxindole-3-N-(cycloheptyl)carboxamide; 1-carbamoyl-7-methyloxindole-3-N-(4-butoxyphenyl)carboxamide; and 1-carbamoyl-7-methyloxindole-3-N-(t-butyl)carboxamide.

EXAMPLE 33

Starting with the appropriate isocyanate and 1-carbamoyloxindole and using the procedure of Example 31, the following compounds are prepared:

[Structure: oxindole with CONHR₁ at 3-position, X and Y substituents, N-C(=O)-NH₂ at N1]

| X | Y | R₁ |
|---|---|---|
| 4-CH₃ | H | [methylthiophene] |
| 4-CH₃ | H | [methylthiophene isomer] |
| 4-CH₃ | H | [methyl isoxazole with CH₃] |
| 4-CH₃CH₂ | H | [pyridine] |
| 4-CH₃CH₂ | H | [dimethylthiophene] |
| 4-CH₃CH₂ | H | [N-methyl imidazole] |
| 5-CH₃ | H | [methylthiophene] |

-continued

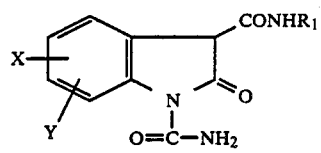

| X | Y | R₁ |
|---|---|---|
| 5-CH₃ | H | (4-methyl-2-furyl) |
| 5-CH₃CH₂CH₂ | H | (4-methyl-2-thiazolyl, 5-CH₃) |
| 5-CH₃CH₂CH₂ | H | (3-thienyl) |
| 5-CH₃(CH₂)₃ | H | (3-furyl) |
| 5-CH₃(CH₂)₃ | H | (1-methyl-5-methyl-2-pyrrolyl) |
| H | 6-CH₃ | (4-methyl-2-isoxazolyl, 5-CH₃) |
| H | 6-CH₃ | (4-methyl-2-thienyl, 5-CH₃) |
| H | 6-CH₃ | (2-methyl-5-methyl pyridyl) |
| H | 6-(CH₃)₂CH | (2-thiazolyl, 5-CH₃) |
| H | 6-(CH₃)₂CH | (thienyl, 5-CH₃, 4-CH₃) |
| H | 7-CH₃ | (4-methyl-2-thienyl, 5-CH₃) |

-continued

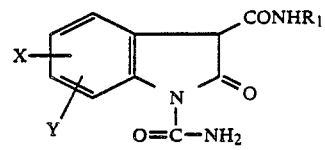

| X | Y | R₁ |
|---|---|---|
| H | 7-CH₃ | (1-methyl-imidazolyl) |
| H | 7-CH₃ | (2-methyl-5-methyl oxazolyl) |

EXAMPLE 34

1-Carbamoyl-5-methoxyoxindole-3-N-(phenyl)carboxamide

Phenylisocyanate (1.43 g., 0.012 mole) is added to a cold solution of 1.92 g. (0.01 mole) of 1-carbamoyl-5-methoxyoxindole and 2.4 g. (0.024 mole) of triethylamine in 25 ml. of dimethylformamide, and the mixture allowed to stir for 2.5 hours. The mixture is added to 400 ml. of 1N hydrochloric acid and allowed to stir for 30 minutes. The solids are filtered, dried and crystallized from acetonitrile to give the desired product.

EXAMPLE 35

Employing the procedure of Example 34 and starting with the requisite isocyanate and 1-carbamoyloxindole, the following compounds are prepared:

1-carbamoyl-4-methoxyoxindole-3-N-(2,5-difluorophenyl)carboxamide; 1-carbamoyl-4-methoxyoxindole-3-N-(t-butyl)carboxamide; 1-carbamoyl-4-methoxyoxindole-3-N-(cyclohexyl)carboxamide; 1-carbamoyl-4-methylthiooxindole-3-N-(2,4-difluorophenyl)carboxamide; 1-carbamoyl-4-methylthiooxindole-3-N-(t-butyl)-carboxamide; 1-carbamoyl-5-ethoxyoxindole-3-N-(3-trifluoromethylphenyl)carboxamide; 1-carbamoyl-5-ethoxyoxindole-3-N-(i-propyl)carboxamide; 1-carbamoyl-5-ethoxyoxindole-3-N-(phenyl)carboxamide; 1-carbamoyl-5-ethoxyoxindole-3-N-(4-butoxyphenyl)carboxamide; 1-carbamoyl-5-n-propythiooxindole-3-N-(3,4-dimethoxyphenyl)carboxamide; 1-carbamoyl-5-n-propyl-thiooxindole-3-N-(2-methoxy-4-ethylphenyl)-carboxamide; 1-carbamoyl-5-n-propylthiooxindole-3-N-(cycloheptyl)carboxamide; 1-carbamoyl-6-methoxyoxindole-3-(2-chloro-4-acetylphenyl)carboxamide; 1-carbamoyl-6-methoxyoxindole-3-N-(4-methoxyphenyl)carboxamide; 1-carbamoyl-6-methoxyoxindole-3-N-(4-propionylphenyl)carboxamide; 1-carbamoyl-6-methylthiooxindole-3-carboxamide; 1-carbamoyl-6-methylthiooxindole-3-N-(t-butyl)carboxamide; 1-carbamoyl-6-methylthiophenyl)carboxamide; 1-carbamoyl-7-methoxyox indole-3-carboxamide; 1-carbamoyl-7-methoxyoxindole-3-N-(3-trifluoromethyl-5-chlorophenyl)carboxamide; 1-carbamoyl-7-methoxyoxindole-3-N-(2-chloro-4-acetylphenyl)carboxamide; 1-carbamoyl-7-n-butylthiooxindole-3-N-(phenyl)carboxamide;

1-carbamoyl-7-n-butylthiooxindole-3-N-(2,4-difluorophenyl)carboxamide; 1-carbamoyl-7-n-butylthiooxindole-3-N-(3,4-dichlorophenyl)carboxamide; and 1-carbamoyl-7-methylthiooxindole-3-N-(2-chloro-4-methylphenyl)carboxamide.

EXAMPLE 36

Starting with the appropriate isocyanate and 1-carbamoyloxindole and using the procedure of Example 34, the following compounds are prepared:

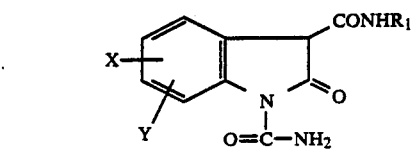

| X | Y | R₁ |
|---|---|---|
| 4-CH₃O | H | 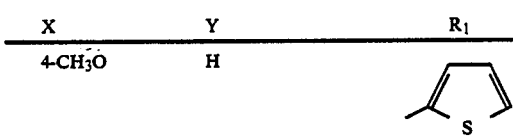 |
| 4-CH₃O | H |  |
| 4-CH₃O | H | 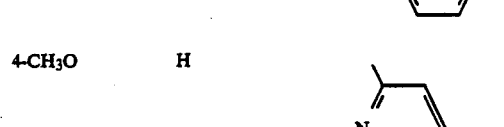 |
| 4-CH₃O | H | 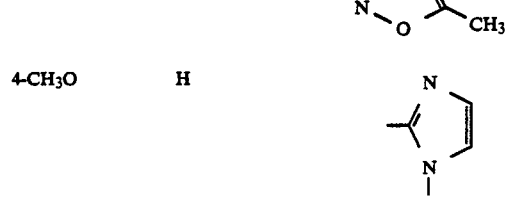 |
| 4-CH₃S | H | 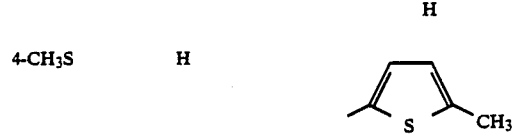 |
| 4-CH₃S | H |  |
| 5-CH₃CH₂O | H |  |
| 5-CH₃CH₂O | H | 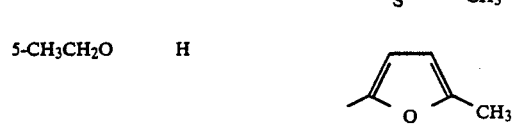 |
| 5-CH₃CH₂O | H | 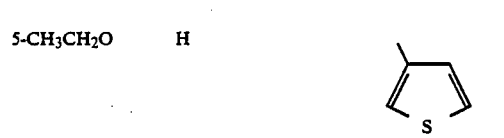 |

-continued

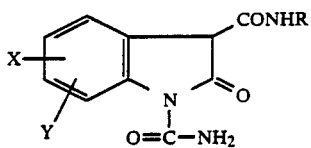

| X | Y | R₁ |
|---|---|---|
| 5-CH₃CH₂O | H | 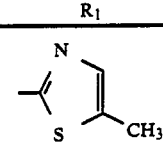 |
| 5-CH₃(CH₂)₂S | H | 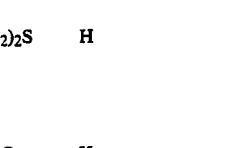 |
| 5-CH₃CH₂O | H | 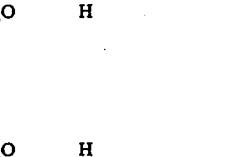 |
| 5-CH₃CH₂O | H | 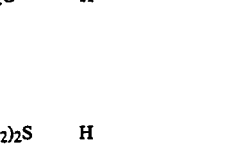 |
| 5-CH₃(CH₂)₂S | H | 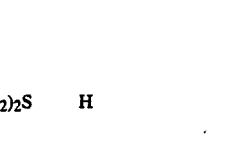 |
| 5-CH₃(CH₂)₂S | H | 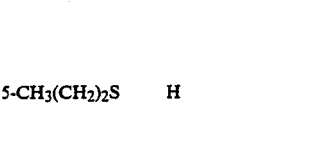 |
| 5-CH₃(CH₂)₂S | H | 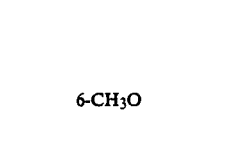 |
| H | 6-CH₃O | 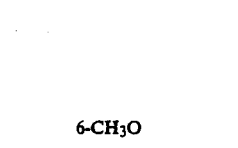 |
| H | 6-CH₃O | 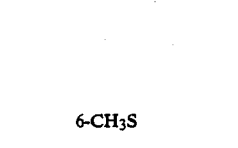 |
| H | 6-CH₃S | 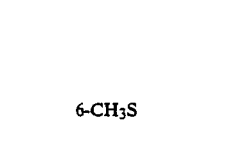 |
| H | 6-CH₃S |  |

-continued

| X | Y | R₁ |
|---|---|---|
| H | 6-CH₃S | 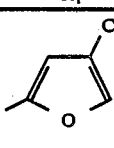 |
| H | 7-CH₃O | 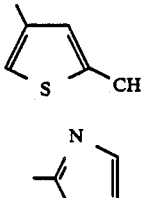 |
| H | 7-CH₃O | 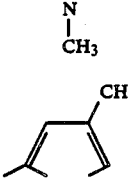 |
| H | 7-CH₃S | 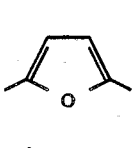 |
| H | 7-CH₃S | 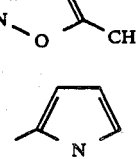 |
| H | 7-CH₃S |  |
| H | 7-CH₃(CH₂)₃S |  |

EXAMPLE 37

1-Carbamoyl-5-cyclohexyloxindole-3-N-(phenyl)carboxamide

Phenylisocyanate (1.43 g., 0.012 mole) is added to a cold solution of 2.45 g. (0.01 mole) of 1-carbamoyl-5-cyclohexyloxindole and 2.4 g. (0.024 mole) of triethylamine in 30 ml. of dimethylformamide, and the reaction stirred for 3 hours. The mixture is poured into 375 ml. of 1N hydrochloric acid and stirred for 30 minutes. The solids are filtered, dried and recrystallized from acetonitrile to give the desired product.

EXAMPLE 38

Using the procedure of Example 37 and starting with the requisite 1-carbamoyloxindole and appropriate isocyanate, the following compounds are prepared.

1-carbamoyl-4-cyclopentyloxindole-3-carboxamide; 1-carbamoyl-4-cyclopentyloxindole-3-N-(i-propyl)carboxamide; 1-carbamoyl-4-cyclohexyloxindole-3-N-(t-butyl)carboxamide; 1-carbamoyl-4-cyclohexyloxindole-3-N-(cyclohexyl)carboxamide; 1-carbamoyl-4-cyclohexyloxindole-3-N-(2,5-difluorophenyl)carboxamide; 1-carbamoyl-4-cyclohexyloxindole-3-N-(2-methoxy-4-ethylphenyl)carboxamide; 1-carbamoyl-5-cyclohexyloxindole-3-N-(2-chloro-4-acetylphenyl)carboxamide; 1-carbamoyl-5-cyclohexyloxindole-3-N-(2,5-difluorophenyl)carboxamide; 1-carbamoyl-5-cyclohexyloxindole-3-N-(2-fluoro-4-methylphenyl)carboxamide; 1-carbamoyl-5-cycloheptyloxindole-3-N-(3,4-dimethoxyphenyl)carboxamide; 1-carbamoyl-5-cycloheptyloxindole-3-N-(2-fluoro-3-chlorophenyl)carboxamide; 1-carbamoyl-5-cycloheptyloxindole-3-N-(cycloheptyl)carboxamide; 1-carbamoyl-6-cyclobutyloxindole-3-carboxamide; 1-carbamoyl-6-cyclobutyloxindole-3-N-(3-trifluoromethyl-5-chlorophenyl)carboxamide; 1-carbamoyl-6-cyclohexyloxindole-3-N-(4-butoxyphenyl)carboxamide; 1-carbamoyl-6-cyclohexyloxindole-3-N-(4-methoxyphenyl)carboxamide; 1-carbamoyl-6-cyclohexyloxindole-3-N-(n-hexyl)carboxamide; 1-carbamoyl-7-cyclopropyloxindole-3-N-(t-butyl)carboxamide; 1-carbamoyl-7-cyclopropyloxindole-3-N-(3,4-diemthylthiophenyl)carboxamide; 1-carbamoyl-7-cyclohexyloxindole-3-N-(cycloheptyl)carboxamide; 1-carbamoyl-7-cyclohexyloxindole-3-N-(2,4-difluorophenyl)carboxamide; 1-carbamoyl-7-cyclohexyloxindole-3-N-(4-propionylphenyl)carboxamide; and 1-carbamoyl-7-cyclohexyloxindole-3-N-(n-hexyl)carboxamide.

EXAMPLE 39

Starting with the requisite isocyanate and appropriate 1-carbamoyloxindole and employing the procedure of Example 37, the following compounds are prepared:

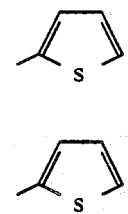

| X and Y Substituent | R₁ |
|---|---|
| H 4- | 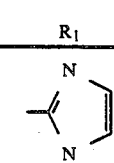 |

EXAMPLE 40

1-Carbamoyl-5,6-dichlorooxindole-3-N-(2,4-dichlorophenyl)carboxamide

To a solution of 500 mg. (2.04 mmoles) of 1-carbamoyl-5,6-dichlorooxindole and 496 mg. (4.9 mmoles) of triethylamine in 20 ml. of dimethylformamide at 5° C. was added 460 mg. (2.45 mmoles) of 2,4-dichloroisocyanate, and the reaction stirred for 3 hours. The reaction was poured into 350 ml. of 1N hydrochloric acid containing ice. After stirring for 30 minutes, the solids were filtered and air dried. Trituration of the solids with hot acetone gave 260 mg. of the desired product, m.p. 231° C., dec.

Anal. Calcd. for $C_{16}H_9O_3N_3Cl_4$: C, 44.4; H, 2.1; N, 9.7. Found: C, 44.3; H, 2.1; N, 9.3.

EXAMPLE 41

1-Carbamoyl-5-fluoro-6-chlorooxindole-3-(4-chlorophenyl)carboxamide

In a manner similar to Example 40, 750 mg. (3.28 mmoles) of 1-carbamoyl-5-fluoro-6-chlorooxindole, 605 mg. (3.9 mmoles) of 4-chlorophenylisocyanate and 1.1 ml. (7.8 mmoles) of triethylamine in 20 ml. of dimethylformamide gave on work-up and recrystallization from acetonitrile 850 mg. of the desired product, m.p. 223° C., dec.

Anal. Calcd. for $C_{16}H_{10}O_3N_3Cl_2F$: C, 50.3; H, 2.6; N, 11.0. Found: C, 50.6; H, 2.8; N, 10.9.

EXAMPLE 42

1-Carbamoyl-5-fluoro-6-chlorooxindole-3-N-(phenyl)-carboxamide

Again, in a manner similar to Example 40, 750 mg. (3.28 mmoles) of 1-carbamoyl-5-fluoro-6-chlorooxindole, 470 mg. (3.9 mmoles) of phenylisocyanate and 1.1 ml. (7.8 mmoles) in 20 ml. of dimethylformamide gave on work-up and crystallization from acetonitrile 525 mg. of the desired product, m.p. 237° C., dec.

Anal. Calcd. for $C_{16}H_{11}O_3N_3ClF$: C, 55.3; H, 3.2; N, 12.1. Found: C, 55.3; H, 3.3; N, 12.1.

EXAMPLE 43

Employing the procedure of Example 40, and starting with the appropriate 1-carbamoyloxindole and requisite isocyanate, the following compounds are prepared:

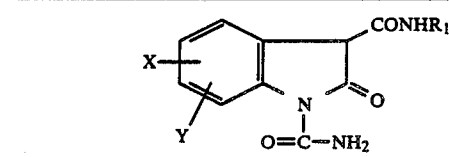

| X | Y | $R_1$ |
|---|---|---|
| 4-F | 6-F |  |
| 4-F | 6-CH₃CH₂S |  |
| 5-F | 6-CH₃O | 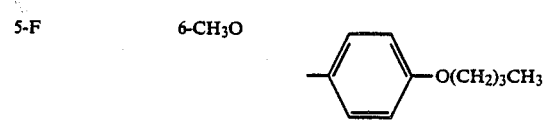 |
| 5-F | 7-F |  |
| 4-F | 6-Cl | —C(CH₃)₃ |
| 4-Cl | 5-CH₃ | 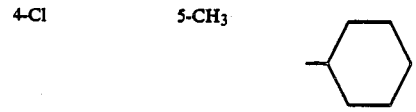 |
| 4-Cl | 7-Cl | 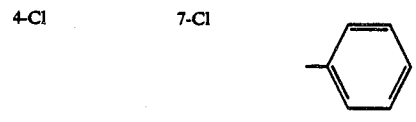 |
| 5-Br | 6-Br | —(CH₂)₅CH₃ |
| 5-Cl | 7-Br |  |

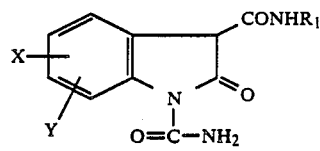

| X | Y | $R_1$ |
|---|---|---|
| 5-F | 6-CH₃CH₂ |  |
| 5-CH₃O | 6-F | 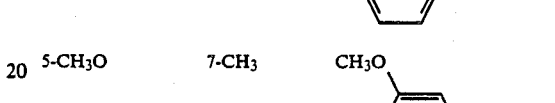 |
| 5-CH₃O | 7-CH₃ |  |
| 5-CH₃CH₂ | 6-CH₃ | 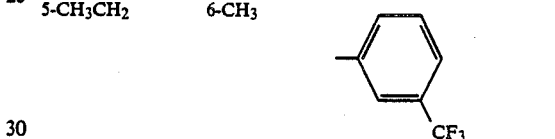 |
| 5-CH₃O | 6-CH₃O | 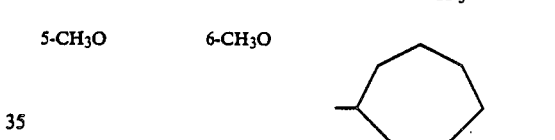 |
| 5-CH₃S | 6-CH₃O | 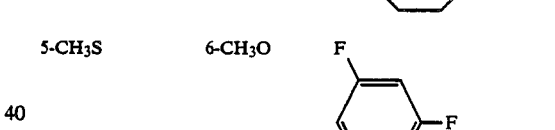 |
| 5-CH₃S | 6-CH₃S | 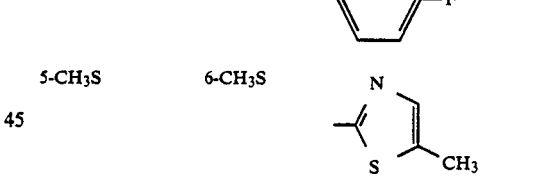 |
| 5-CH₃S | 6-CH₃S | —CH(CH₃)₂ |
| 5-CH₃(CH₂)₃— | 7-F | 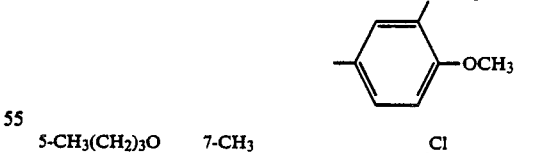 |
| 5-CH₃(CH₂)₃O | 7-CH₃ | 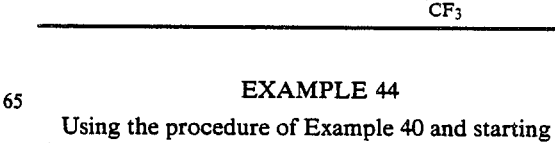 |

EXAMPLE 44

Using the procedure of Example 40 and starting with the appropriate isocyanate and 1-carbamoyloxindole, the following products are prepared:

1-carbamoyl-5-chloro-6-trifluoromethyloxindole-3-N-(2-thienyl)carboxamide; 1-carbamoyl-5-fluoro-6-trifluoromethyloxindole-3-N-(2,4-difluorophenyl)carboxamide; 1-carbamoyl-4-methyl-6-trifluoromethyloxindole-3-N-(2-pyridyl)carboxamide; 1-carbamoyl-5-trifluoromethyl-7-methoxyoxindole-3-N-(4-methoxyphenyl)carboxamide; 1-carbamoyl-5-trifluoromethyl-6-methylthiooxindole-3-N-(2-chloro-4-acetylphenyl)carboxamide; 1-carbamoyl-4-trifluoromethyl-6-n-propyloxindole-3-N-(3-thienyl)carboxamide; 1-carbamoyl-4-trifluoromethyl-6-n-propylthiooxindole-3-N-(5-methyl-2-thiazolyl)carboxamide; 1-carbamoyl-4-trifluoromethyl-6-n-propoxyoxindole-3-N-(2-methoxy-4-ethylphenyl)carboxamide; 1-carbamoyl-4-trifluoromethyl-5-methyloxindole-3-N-(1-methyl-2-imidazolyl)carboxamide; 1-carbamoyl-5-trifluoromethyl-7-bromooxindole-3-N-(2,5-difluorophenyl)carboxamide; 1-carbamoyl-4-methyl-6-trifluoromethyloxindole-3-N-(4-propionylphenyl)carboxamide; 1-carbamoyl-5-n-butyl-7-trifluoromethyloxindole-3-N-(2-fluoro-3-chlorophenyl)carboxamide; 1-carbamoyl-5-bromo-7-trifluoromethyloxindole-3-N-(n-hexyl)carboxamide; 1-carbamoyl-5-methylthio-7-trifluoromethyloxindole-3-N-(2-chloro-4-acetylphenyl)carboxamide; 1-carbamoyl-4-fluoro-7-trifluoromethyloxindole-3-N-(cycloheptyl)carboxamide; and 1-carbamoyl-5-methyl-6-trifluoromethyloxindole-3-N-(2,5-difluorophenyl)carboxamide.

EXAMPLE 45

The procedure of Example 40 is again repeated, starting with the appropriate 1-carbamoyloxindole and isocyanate, to give the following compounds:

1-carbamoyl-4-fluoro-5-nitrooxindole-3-N-(2,4-difluorophenyl)carboxamide; 1-carbamoyl-4-methyl-5-nitrooxindole-3-N-(cyclohexyl)carboxamide; 1-carbamoyl-4-chloro-5-nitrooxindole-3-N-(3,4-dimethoxyphenyl)carboxamide; 1-carbamoyl-4-methyl-5-acetyloxindole-3-N-(3-trifluoromethylphenyl)carboxamide; 1-carbamoyl-4-chloro-5-acetyloxindole-3-N-(2-chloro-4-acetylphenyl)carboxamide; 1-carbamoyl-4-methoxy-6-butyryloxindole-3-N-(5-methyl-2-thiazolyl)carboxamide; 1-carbamoyl-4-fluoro-6-acetyloxindole-3-N-(2-methoxy-4-ethylphenyl)carboxamide; 1-carbamoyl-5-methyl-7-acetyloxindole-3-N-(cycloheptyl)carboxamide; 1-carbamoyl-5-methylthio-7-acetyloxindole-3-N-(5-methyl-1-2-isoxazolyl)carboxamide; 1-carbamoyl-4-chloro-6-benzoyloxindole-3-N-(2,5-difluorophenyl)carboxamide; 1-carbamoyl-4-methoxy-6-benzoyloxindole-3-N-(2-thienyl)carboxamide; 1-carbamoyl-5-ethylthio-7-benzoyloxindole-3-N-(2-fluoro-3-chlorophenyl)carboxamide; 1-carbamoyl-4-fluoro-6-(2-thenoyl)oxindole-3-N-(1-methyl-2-imidazolyl)carboxamide; 1-carbamoyl-4-methyl-6-(2-thenoyl)oxindole-3-N-(2-chloro-4-acetylphenyl)carboxamide; 1-carbamoyl-4-methylthio-6-(3-thenoyl)oxindole-3-N-(2-thienyl)carboxamide; and 1-carbamoyl-5-bromo-7-(2-thenoyl)oxindole-3-N-(2-pyridyl)carboxamide.

EXAMPLE 46

1-N-(4-methoxypenyl)carbamoyl-5-chlorooxindole-3-N-(2,4-dichlorophenyl)carboxamide To a solution of 1.0 g. (3.15 mmoles) of 1-N-(4-methoxyphenyl)carbamoyl-5-chlorooxindole and 1.06 ml. (7.6 mmoles) of triethylamine in 20 ml. of dimethylformamide cooled to 0°–5° C. was added 712 mg. (3.78 mmoles) of 2,4-dichlorophenylisocyanate, and the reaction mixture stirred for 1 hour. The reaction mixture was poured into 50 ml. of 1N hydrochloric acid 50 ml. of water and 50 ml. of methanol, and allowed to stir for 30 minutes. The solids were filtered and dried to give 600 mg. of the desired product, m.p. 253°–255° C., dec.

Anal. Calcd. for $C_{23}H_{16}O_4N_3Cl_3$: C, 54.7; H, 3.2; N, 8.3. Found: C, 54.3; H, 3.2; N, 8.2.

EXAMPLE 47

Using the procedure of Example 46 and starting with the appropriate 1-carbamoyloxindole and isocyanate, the following compounds were prepared:

| X | Y | $R_2$ | $R_1$ | m.p. °C. |
|---|---|---|---|---|
| H | H | 4-methoxyphenyl | 2-thienyl | 183 dec. |
| H | H | 4-methoxyphenyl | 2,4-dichlorophenyl | 203 dec. |

EXAMPLE 48

1-N-(Phenyl)carbamoyl-5-chlorooxindole-3-N-(2-thiazolyl)carboxamide

A solution of 1.0 g. (2.9 mmoles) of methyl 1-N-(phenyl)carbamoyl-5-chlorooxindole-3-carboxylate and 581 mg. (5.8 mmoles) of 2-aminothiazole in 100 ml. of toluene was heated to reflux overnight using a soxhlet extractor containing about 4 ml. of 4A molecular sieves. The reaction mixture was poured into 300 ml. of 1N hydrochloric acid and allowed to stir for 30 minutes. The solids were filtered and recrystallized from dimethylformamide—water and then from acetonitrile, 600 mg., m.p. 241° C., dec.

Anal Calcd. for $C_{19}H_{13}O_3N_4ClS$: C, 55.3; H, 3.2; N, 13.6. Found: C, 55.1; H, 2.9; N, 13.8.

EXAMPLE 49

1-N-(Phenyl)carbamoyl-5-chlorooxindole-3-N-(2-pyridyl)carboxamide

A solution consisting of 1.0 g. (2.9 mmoles) of methyl 1-N-(phenyl)carbamoyl-5-chlorooxindole-3-carboxylate and 546 mg. (5.8 mmoles) of 2-aminopyridine in 100 ml. of toluene was heated to reflux overnight using a soxhlet extractor containing about 4 ml. of 4A molecular sieves. The reaction mixture was cooled and poured into 300 ml. of 1N hydrochloric acid. After stirring for 30 minutes the solids were filtered, washed with water and recrystallized from dimethylformamide—water, 800 mg., m.p. 274° C., dec.

Anal. Calcd. for $C_{21}H_{15}O_3N_4Cl$: C, 62.0; H, 3.7; N, 13.8. Found: C, 61.8; H, 3.7; N, 13.7.

EXAMPLE 50

Starting with the appropriate alkyl 1-carbamoyloxindole-3-carboxylate and amine and employing the procedure of Example 48, the following compounds are prepared:
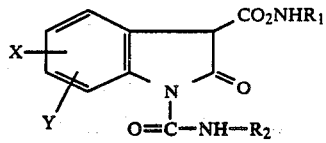
| X | Y | R₁ | R₂ |
|---|---|---|---|
| 4-Cl | H | 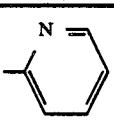 | 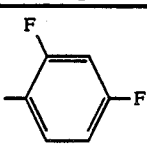 |
| 4-F | H | 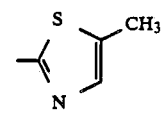 | 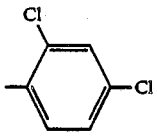 |
| 5-Br | H | 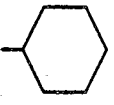 |  |
| 5-Br | H | H | 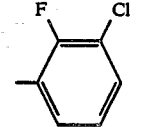 |
| H | 6-F | —(CH₂)₄CH₃ | 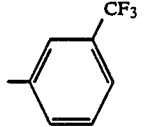 |
| 4-CH₃ | H | 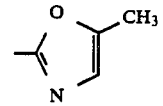 | 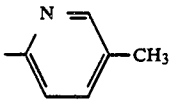 |
| H | 6-CF₃ | H | H |
| H | 5-φCO | H | H |
| H | 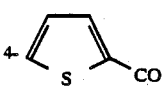 | H | H |
| H | 5-NO₂ | H | H |
| H | 6-(CH₃)₂CH | 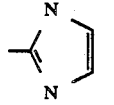 | 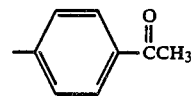 |
| H | 7-CH₃ | 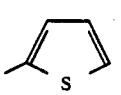 | 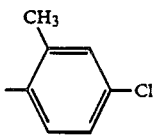 |

-continued

[Structure: indoline-2-one with X substituent on benzene ring, Y substituent, 3-position has CO₂NHR₁, N-1 has C(=O)NH-R₂]

| X | Y | R₁ | R₂ |
|---|---|---|---|
| 4-OCH₃ | H | 5-methyl-2-furyl (attached via CH₃ group on furan) | 5-methyl-2-thienyl |
| 5-CH₃CH₂O | H | 4-ethoxyphenyl | 3-methyl-2-thienyl |
| H | 6-OCH₃ | 2,3-dimethylphenyl | 1-methyl-2-pyrrolyl |
| 4-SCH₃ | H | 4-cyclopropylcyclohexyl | 4-(methylthio)phenyl |
| 5-S(CH₂)₂CH₃ | H | 3-chloro-5-(trifluoromethyl)phenyl | 2-methoxy-4-methoxyphenyl |
| H | 6-SCH₃ | phenyl | H |
| H | 7-S(CH₂)₃CH₃ | —CH(CH₃)₂ | cyclohexyl |
| H | 4-CH₃ | H | H |
| H | 4-CH₃S | H | H |
| H | 4-cyclopropyl | H | H |
| 5-C₂H₅O | 7-CH₃ | H | H |
| 5-φCO | 7-CH₃ | H | H |

EXAMPLE 51

1-N-Phenylcarbamoyl-5-Acetyloxindole-3-N-(2,4-difluorophenyl)carboxamide

To 1.0 g. (3.4 mmoles) of 1-N-phenylcarbamoyl-5-acetyloxindole in 35 ml. of dimethylformamide at 0°–5° C. was added 1.1 ml. (10.8 mmoles) of triethylamine followed by 620 mg. (4 mmoles) of 2,4-difluorophenylisocyanate, and the reaction mixture allowed to stir for 2 hours in the cold. The mixture was poured into 300 ml. of 1N hydrochloric acid and allowed to stir for 30 minutes. The solids were filtered, washed with water and air dried. Recrystallization from acetonitrile gave 900 mg. of product, m.p. 208° C., dec. Anal. Calcd. for $C_{24}H_{17}O_4N_3F_2$: C, 64.1; H, 3.8; N, 9.4. Found: C, 64.1; H, 3.9; N, 9.4.

EXAMPLE 52

Employing the procedure of Example 51 and starting with the requisite isocyanate and 1-carbamoyloxindole, the following compounds were prepared:

1-N-Phenyl-5-benzoyloxindole-3-N-phenylcarboxamide, m.p. 212° C., dec.

Anal. Calcd. for $C_{29}H_{21}O_4N_3$: C, 73.3; H, 4.5; N, 8.8. Found: C, 73.2; H, 4.4; N, 8.8.

1-N-Phenylcarbamoyl-5-(2-thenoyl)oxindole-3-N-(4-chlorophenyl)carboxamide, m.p. 222° C., dec.

Anal. Calcd. for $C_{27}H_{18}O_4N_3ClS$: C, 62.9; H, 3.5; N, 8.1. Found: C, 62.6; H, 3.6; N, 8.1.

1-N-Phenylcarbamoyl-5-(2-thenoyl)oxindole-3-N-phenylcarboxamide, m.p. 203° C., dec.

Anal. Calcd. for $C_{27}H_{19}O_4N_3S$: C, 67.4; H, 4.0; N, 8.7. Found: C, 67.2; H, 4.1; N, 8.7.

1-N-Phenylcarbamoyl-5-acetyloxindole-3-N-(4-chlorophenyl)carboxamide, m.p. 210° C., dec.

Anal. Calcd. for $C_{24}H_{18}O_4N_3Cl$: C, 64.4; H, 4.1; N, 9.4. Found: C, 64.3; H, 4.0; N, 9.3.

1-N-Phenylcarbamoyl-5-acetyloxindole-3-N-phenylcarboxamide, m.p. 202° C., dec.

Anal. Calcd. for $C_{24}H_{19}O_4N_3$: C, 69.7; H, 4.6; N, 10.2. Found: C, 69.5; H, 4.5; N, 10.1.

1-N-Phenylcarbamoyl-5-benzoyloxindole-3-N-(4-chlorophenyl)carboxamide, m.p. 229° C., dec.

Anal. Calcd. for $C_{29}H_{20}O_4N_3Cl$: C, 68.3; H, 4.0; N, 8.2. Found: C, 68.3; H, 4.0; N, 8.2.

1-N-(4-Fluorophenyl)carbamoyl-6-benzoyloxindole-3-N-(4-fluorophenyl)carboxamide, m.p. 210°-212° C., dec.

Anal. Calcd. for $C_{29}H_{19}O_4N_3F_2$: C, 68.1; H, 3.7; N, 8.2. Found: C, 67.9; H, 3.8; N, 8.2.

EXAMPLE 53

Starting with the requisite 1-carbamoyloxindole and isocyanate and using the procedure of Example 51, the following compounds are prepared:

1-N-phenylcarbamoyl-4-acetyloxindole-3-N-(2,4-difluorophenyl)carboxamide; 1-N-n-propyl-4-acetyloxindole-3-N-(2-pyridyl)carboxamide; 1-N-cycloheptyl-5-propionyloxindole-3-N-(2-chloro-4-methylphenyl)carboxamide; 1-N-(3-trifluoromethylphenyl)carbamoyl-6-butyryloxindole-3-N-(5-methyl-2-thiazolyl)carboxamide; 1-N-(2,4-dichlorophenyl)carbamoyl-7-propionyloxindole-3-N-(2-thienyl)carboxamide; 1-N-(2,4-dimethoxyphenyl)carbamoyl-5-benzoyloxindole-3-N-(4-cyclopropylphenyl)carboxamide; 1-N-(2-fluoro-3-chlorophenyl)carbamoyl-5-benzoyloxindole-3-N-(2-methoxy-4-ethylphenyl)carboxamide; 1-N-(4-butoxyphenyl)carbamoyl-6-benzoyloxindole-3-N-(5-methyl-2-furyl)carboxamide; 1-N-(cyclohexyl)carbamoyl-7-benzoyloxindole-3-N-(3-thienyl)carboxamide; 1-N-(3-trifluoromethyl-5-chlorophenyl)carbamoyl-5-(2-thenoyl))oxindole-3-N-phenylcarboxamide; 1-N-(3,4-dimethoxyphenyl)-6-(3-thenoyl)oxindole-3-N-(4-propionylphenyl)carboxamide; 1-N-(cycloheptyl)carbamoyl-6-(2-thenoyl)oxindole-3-N-(4-methoxyphenyl)carboxamide; and 1-N-(n-butyl)carbamoyl-7-(2-thenoyl)oxindole-3-N-(4-propionylphenyl)carboxamide.

EXAMPLE 54

1-N-Phenylcarbamoyl-5-nitrooxindole-3-N-phenylcarboxamide

To a solution of 1.0 g. (3.4 mmoles) of 1-N-phenylcarbamoyl-5-nitrooxindole in 25 ml. of dimethylformamide at 0°-5° C. was added 0.44 ml. of (4 mmoles) of phenylisocyanate and 1.13 ml. (8 mmoles) of triethylamine, and the resulting reaction mixture allowed to stir for one hour. The reaction mixture was poured into 300 ml. of 1N hydrochloric acid and allowed to stir for 20 minutes. The solids were filtered, washed with water, dried and recrystallized from ethyl acetate, 400 mg., m.p. 219° C., dec.

Anal. Calcd. for $C_{22}H_{16}O_5N_4$: C, 63.5; H, 3.9; N, 13.5. Found: C, 63.6; H, 3.9; N, 13.5.

EXAMPLE 55

Using the procedure of Example 54 and starting with the appropriate 1-carbamoyloxindole and isocyanate, the following compounds are prepared:

1-N-(2-furylmethyl)carbamoyloxindole-3-N-phenylcarboxamide; 1-N-(3-thienylmethyl)carbamoyloxindole-3-N-phenylcarboxamide; 1-N-(t-butyl)carbamoyl-4-nitrooxindole-3-N-(2,4-dichlorophenyl)carboxamide; 1-N-(cycloheptyl)carbamoyl-4-nitrooxindole-3-N-(4-butoxyphenyl)carboxamide; 1-N-(2-pyridyl)carbamoyl-4-nitrooxindole-3-carboxamide; 1-N-(2-chloro-4-acetylphenyl)carbamoyl-5-nitrooxindole-3-N-(2-thienyl)carboxamide; 1-N-(2-furyl)carbamoyl-5-nitrooxindole-3-N-(2-fluoro-4-methylphenyl)carboxamide; 1-N-(2-methoxy-4-ethylphenyl)carbamoyl-5-nitrooxindole-3-N-(cyclohexyl)carboxamide; 1-N-(3,4-dimethoxyphenyl)carbamoyl-6-nitrooxindole-3-N-(4-methylthiophenyl)carboxamide; 1-N-(5-methyl-2-furyl)carbamoyl-6-nitrooxindole-3-N-(1-methyl-2-imidazolyl)carboxamide; 1-N-(3-trifluoromethyl-5-chlorophenyl)carbamoyl-6-nitrooxindole-3-N-(4-acetylphenyl)carboxamide; 1-N-(4-butoxyphenyl)carbamoyl-7-nitrooxindole-3-N-(2,4-difluorophenyl)carboxamide; 1-N-(2-chloro-4-acetylphenyl)carbamoyl-4-trifluoromethyloxindole-3-N-(2-methoxy-4-ethylphenyl)carboxamide; 1-N-(4-methoxyphenyl)carbamoyl-5-trifluoromethyloxindole-3-N-(5-methyl-2-oxazolyl)carboxamide; 1-N-(4-propionylphenyl)carbamoyl-5-trifluoromethyloxindole-3-N-(5-methyl-2-furyl)carboxamide; 1-N-(2-fluoro-3-chlorophenyl)carbamoyl-6-trifluoromethyloxindole-3-N-(2,4-difluorophenyl)carboxamide; 1-N-(thenyl)carbamoyl-7-trifluoromethyloxindole-3-N-(1-methyl-2-pyrrolyl)carboxamide; and 1-N-(3,4-dimethoxyphenyl)carbamoyl-7-trifluoromethyloxindole-3-N-(5-methyl-3-isoxazolyl)carboxamide.

EXAMPLE 56

1-N-(4-methoxyphenyl)carbamoyl-5-cyclohexyloxindole-3-N-(phenyl)carboxamide

Phenylisocyanate (1.43 g., 0.012 mole) is added to a cold solution of 3.64 g. (0.01 mole) of 1-N-(4-methoxyphenyl)carbamoyl-5-cyclohexyloxindole and 2.4 g. (0.024 mole) of triethylamine in 30 ml. of dimethylformamide, and the reaction mixture allowed to stir for 2 hours. The mixture is poured into 300 ml. of 1N hydrochloric acid and stirred for 20 minutes. The solids are filtered, dried and recrystallized from ethyl acetate.

EXAMPLE 57

Employing the proceudre of Example 56 and starting with the appropriate 1-carbamoyloxindole and isocyanate, the following compounds are prepared:

1-N-phenylcarbamoyl-4-cyclopentyloxindole-3-carboxamide; 1-N-(2,4-difluorophenyl)carbamoyl-4-cyclohexyloxindole-3-N-(i-propyl)carboxamide; 1-N-(2-thienyl)carbamoyl-4-cyclohexyloxindole-3-N-(cycloheptyl)carboxamide; 1-N-(3,4-dimethylthiophenyl)carbamoyl-5-cyclohexyloxindole-3-N-(3,4-dimethoxyphenyl)carboxamide; 1-N-(2-fluoro-4-methylphenyl)carbamoyl-5-cycloheptyloxindole-3-N-(4-acetylphenyl)carboxamide; 1-N-(t-butyl)carbamoyl-6-cyclohexyloxindole-3-N-(2-chloro-4-acetylphenyl)carboxamide; 1-N-(5-methyl-2-thiazolyl)carbamoyl-6- cyclohexyloxindole-3-N-(4-propionylphenyl)carboxamide; 1-N-(cyclohexyl)carbamoyl-7-cyclopropyloxindole-3-N-(3-trifluoromethyl-5-chlorophenyl)carboxamide; 1-N-(5-methyl-2-furyl)carbamoyl-7-cyclopropyloxindole-3-N-(n-hexyl)carboxamide; 1-N-(4-butoxyphenyl)carbamoyl-7-cyclohexyloxindole-3-N-(4-methoxyphenyl)carboxamide; 1-N-(4-cyclopropylphenyl)-7-cyclohexyloxindole-3-N-(2,5-difluorophenyl)carboxamide; and 1-N-(2-isoxazolyl)-7-cyclohexyloxindole-3-N-(phenyl)carboxamide.

EXAMPLE 58

1-N-(4-Methoxyphenyl)carbamoyl-5-chloro-6-fluorooxindole-3-N-(phenyl)carboxamide To a solution of 3.35 g. (0.01 mole) of 1-N-(4-methoxyphenyl)carbamoyl-5-chloro-6-fluorooxindole in 35 ml. of dimethylformamide cooled to 0°–5° C. is added 2.4 g. (0.24 g mole) of triethylamine followed by 1.43 g. (0.012 mole) of phenylisocyanate, and the resulting reaction mixture allowed to stir for 3 hours. The mixture is poured into 350 ml. of 1N hydrochloric acid and allowed to stir for 20 minutes. The solids are filtered, dried and recrystallized from ethyl acetate.

EXAMPLE 59

Employing the procedure of Example 58 and starting with the appropriate reagents, the following compounds are prepared:
1-N-(i-propyl)carbamoyl-4,6-difluorooxindole-3-N-(phenyl)carboxamide; 1-N-(3-trifluoromethyl-5-chlorophenyl)carbamoyl-4-fluoro-6-ethylthiooxindole-3-N-(2-thienyl)carboxamide; 1-N-(cycloheptyl)carbamoyl-5-fluoro-6-methoxyoxindole-3-N-(4-propionylphenyl)carboxamide; 1-N-(5-methyl-2-furyl)carbamoyl-5,7-difluorooxindole-3-N-(n-hexyl)carboxamide; 1-N-(2-methoxy-4-ethylphenyl)carbamoyl-4-fluoro-6-chlorooxindole-3-N-(5-methyl-3-isoxazolyl)carboxamide; 1-N-(2,4-difluorophenyl)carbamoyl-4-chloro-5-methyloxindole-3-N-(3-trifluoromethylphenyl)carboxamide; 1-N-(3,4-dimethoxyphenyl)carbamoyl-4,7-dichlorooxindole-3-N-(3-pyridyl)carboxamide; 1-N-(5-methyl-2-thiazolyl)carbamoyl-5-fluoro-6-bromooxindole-3-N-(4-butoxyphenyl)carboxamide; 1-N-(2-fluoro-3-chlorophenyl)carbamoyl-5,6-dibromooxindole-3-N-(cyclohexyl)carboxamide; 1-N-(2-chloro-4-acetylphenyl)carbamoyl-5-chloro-7-bromooxindole-3-N-(1-methyl-2-imidazolyl)carboxamide; 1-N-(2,4-dichlorophenyl)carbamoyl-5-fluoro-6-ethyloxindole-3-N-(5-methyl-2-furyl)carboxamide; 1-N-(cycloheptyl)carbamoyl-5-methoxy-7-methyloxindole-3-N-(2,4-dichlorophenyl)carboxamide; 1-N-(2-methoxy-4-ethylphenyl)carbamoyl-5-ethyl-6-methyloxindole-3-N-(3-trifluoromethylphenyl)carboxamide; 1-N-(4-propionylphenyl)carbamoyl-5,6-dimethoxyoxindole-3-N-(cycloheptyl)carboxamide; 1-N-(4-chlorophenyl)carbamoyl-5-methylthio-6-methoxyoxindole-3-N-(4-fluorophenyl)carboxamide; 1-N-(4-methoxyphenyl)carbamoyl-5-ethoxy-7-methyloxindole-3-N-(3-thienyl)carboxamide; 1-N-(4-acetylphenyl)carbamoyl-5,6-dimethylthiooxindole-3-N-(4-methylphenyl)carboxamide; 1-N-(4-bromophenyl)carbamoyl-5-n-butyl-7-fluorooxindole-3-N-(t-butyl)carboxamide; 1-N-(2-thienyl)carbamoyl-5-n-hexyl)carboxamide; and 1-N-(2,4-dichlorophenyl)carbamoyl-4-chloro-6-n-butylthiooxindole-3-N-(4-cyclopropylphenyl)carboxamide.

EXAMPLE 60

1-N-(4-Methoxyphenyl)carbamoyl-6-chloro-7-trifluoromethyloxindole-3-N-(phenyl)carboxamide To 35 ml. of dimethylformamide cooled to 0°–5° C. and containing 3.85 g. (0.01 mole) of 1-N-(4-methoxyphenyl)carbamoyl-5-chloro-6-(trifluoromethyloxindole is added 2.4 g. (0.024 mole) of triethylamine followed by 1.43 g. (0.012 mole) of phenylisocyanate, and the resulting reaction mixture allowed to stir for 3 hours. The mixture is poured into 300 ml. of 1N hydrochloric acid and allowed to stir for 30 minutes. The solids are filtered, dried and recrystallized from ethyl acetate.

EXAMPLE 61

Starting with the requisite reagents and using the procedure of Example 60, the following compounds are prepared:
1-N-(i-propyl)carbamoyl-5-chloro-6-trifluoromethyloxindole-3-N-(cycloheptyl)carboxamide; 1-N-(2,4-difluorophenyl)carbamoyl-4-methyl-6-trifluoromethyloxindole-3-N-(4-butoxyphenyl)carboxamide; 1-N-(cyclohexyl)carbamoyl-5-trifluoromethyl-6-methoxyoxindole-3-N-(4-acetylphenyl)carboxamide; 1-N-(2-thienyl)carbamoyl-5-trifluoromethyl-6-methylthiooxindole-3-N-(2-fluoro-3-chlorophenyl)carboxamide; 1-N-(3-trifluoromethylphenyl)carbamoyl-4-trifluoromethyl-6-n-propylthiooxindole-3-N-(5-methyl-2-thiazolyl)carboxamide; 1-N-(n-hexyl)carbamoyl-4-trifluoromethyl-6-n-propoxyoxindole-3-N-(2-fluoro-3-chlorophenyl)carboxamide; 1-N-(2-chloro-4-acetylphenyl)carbamoyl-4-trifluoromethyl-5-methyloxindole-3-N-(2-pyridyl)carboxamide; 1-N-(2,5-difluorophenyl)carbamoyl-5-trifluoromethyl-7-bromooxindole-3-N-(2-furyl)carboxamide; 1-N-(1-methyl-2-pyrrolyl)carbamoyl-4-methyl-6-trifluoromethyloxindole-3-N-(5-methyl-2-oxazolyl)carboxamide; 1-N-(2-thienyl)carbamoyl-5-n-butyl-7-trifluoromethyloxindole-3-N-(2-methoxy-4-ethylphenyl)carboxamide; 1-N-(cyclohexyl)carbamoyl-5-methoxy-7-trifluoromethyloxindole-3-N-(4-cyclopropylphenyl)carboxamide; 1-N-(2-chloro-4-acetylphenyl)carbamoyl-5-bromo-7-trifluoromethyloxindole-3-N-(cycloheptyl)carboxamide; 1-N-(4-chlorophenyl)carbamoyl-5-methylthio-7-trifluoromethyloxindole-3-N-(4-methoxyphenyl)carboxamide; 1-N-(cycloheptyl)carbamoyl-4-fluoro-7-trifluoromethyloxindole-3-N-(2-methoxy-4-ethylphenyl)carboxamide; and 1-N-(2,4-dichlorophenyl)carbamoyl-5-methyl-6-trifluoromethyloxindole-3-N-(4-chlorophenyl)carboxamide.

EXAMPLE 62

1-N-(Phenyl)carbamoyl-5-nitro-6-fluorooxindole-3-N-(4-chlorophenyl)carboxamide

To 3.15 g (0.01 mole) of 1-N-(phenyl)carbamoyl-5-nitro-6-fluorooxindole in 35 ml. of dimethylformamide cooled to 0°–5° C. is added 2.4 g (0.024 mole) of triethylamine followed by 1.84 g. (0.012 mole) of 4-chlorophenylisocyanate, and the resulting reaction mixture allowed to stir for 3 hours. The mixture is poured into 325 ml. of 1N hydrochloric acid and allowed to stir for 25 minutes. The solids are filtered, washed with 25 ml. of water, dried and recrystallized from ethyl acetate.

EXAMPLE 63

Using the procedure of Example 62 and starting with the appropriate 1-carbamoyloxindole and requisite isocyanate, the following compounds are prepared:

1-N-(i-propyl)carbamoyl-4-fluoro-5-nitrooxindole-3-N-(2,4-difluorophenyl)carboxamide; 1-N-(cycloheptyl)-carbamoyl-4-carbamoyl-4-methyl-5-nitrooxindole-3-N-(2-pyridyl)carboxamide; 1-N-(2-chloro-4-acetylphenyl)carbamoyl-4-chloro-5-nitrooxindole-3-N-(5-methyl-2-thiazolyl)carboxamide; 1-N-(3-trifluoromethylphenyl)carbamoyl-5-fluoro-6-nitrooxindole-3-N-(3,4-dimethoxyphenyl)carboxamide; 1-N-(4-cyclopropylphenyl)carbamoyl-4-methyl-5-acetyloxindole-3-N-(cycloheptyl)carboxamide; 1-N-(4-acetylphenyl)carbamoyl-4-chloro-5-acetyloxindole-3-N-(2-thienyl)carboxamide; 1-N-(4-methoxyphenyl)carbamoyl-4-methoxy-6-butyryloxindole-3-N-(n-hexyl)carboxamide; 1-N-(5-methyl-2-isoxazolyl)carbamoyl-4-fluoro-6-acetyloxindole-3-N-(2-furyl)carboxamide; 1-N-(2-pyridyl)carbamoyl-5-methyl-7-acetyloxindole-3-N-(2-methoxy-4-ethylphenyl)carboxamide; 1-N-(1-methyl-2-pyrrolyl)carbamoyl-5-methylthio-7-acetyloxindole-3-N-(5-methyl-2-furyl)carboxamide; 1-N-(cyclohexyl)-carbamoyl-4-chloro-6-benzoyloxindole-3-N-(2-fluoro-3-chlorophenyl)carboxamide; 1-N-(1-methyl-2-imidazolyl)carbamoyl-4-methoxy-6-benzoyloxindole-3-N-(3-thienyl)carboxamide; 1-N-(4-cyclohexylphenyl)-carbamoyl-5-fluoro-7-benzoyloxindole-3-N-(2-oxazolyl)carboxamide; 1-N-(4-methylthiophenyl)carbamoyl-5-ethylthio-7-benzoyloxindole-3-N-(cycloheptyl)carboxamide; 1-N-(n-hexyl)carbamoyl-4-fluoro-6-(2-thenoyl)oxindole-3-N-(t-butyl)carboxamide; 1-N-(2,5-difluorophenyl)carbamoyl-4-methyl-6-(2-thenoyl-)oxindole-3-N-(2-chloro-4-acetylphenyl)carboxamide; and 1-N(cycloheptyl)carbamoyl-5-bromo-7-(2-thenoyl-)oxindole-3-N-(2,5-difluorophenyl)carboxamide.

EXAMPLE 64

1-N-(4-Methoxyphenyl)carbamoyl-5,6-methylenedioxyoxindole-3-N-(2-thienyl)carboxamide To a solution of 3.44 g. (0.01 mole) of 1-N-(4-methoxyphenyl)carbamoyl-5,6-methylenedioxyoxindole and 2.4 g. (0.024 mole) of triethylamine in 40 ml. of dimethylformamide cooled to 0°–5° C. is added 1.5 g. (0.012 mole) of 2-thienylisocyanate, and the resulting reaction mixture allowed to stir for 3 hours. The mixture is added to 350 ml. of 1N hydrochloric acid and allowed to stir for 20 minutes. The solids are filtered, dried and recrystallized from acetonitrile.

EXAMPLE 65

Starting with the appropriate 1-carbamoyloxindole and requisite isocyanate and employing the procedure of Example 64, the following compounds are prepared:

1-carbamoyl-5,6-methylenedioxyoxindole-3-N-(2,4-difluorophenyl)carboxamide; 1-N-(4-chlorophenyl)carbamoyl-4,5-methylenedioxyoxindole-3-N-(2-furyl)carboxamide; 1-N-(3-trifluoromethylphenyl)carbamoyl-4,5-methylenedioxyoxindole-3-N-(cycloheptyl)carboxamide; 1-N-(i-propyl)carbamoyl-4,5-methylenedioxyoxindole-3-N-(4-butoxyphenyl)carboxamide; 1-N-(3,4-dimethoxyphenyl)carbamoyl-4,5-methylenedioxyoxindole-3-N-(n-hexyl)carboxamide; 1-N-(2-methoxy-4-ethylphenyl)carbamoyl-5,6-methylenedioxyoxindole-3-N-(4-cyclopropylphenyl)carboxamide; 1-N-(4-fluorophenyl)carbamoyl-5,6-methylenedioxyoxindole-3-N-(2-pyridyl)carboxamide; 1-N-(4-acetylphenyl)carbamoyl-5,6-methylenedioxyoxindole-3-N-(5-methyl-2-isoxazolyl)carboxamide; 1-N-(2-pyridyl)carbamoyl-5,6-methylenedioxyoxindole-3-N-(phenyl)carboxamide; 1-carbamoyl-4,5-methylenedioxyoxindole-3-N-(2,4-dichlorophenyl)carboxamide; 1-N-(t-butyl)carbamoyl-5,6-methylenedioxyoxindole-3-N-(2-chloro-4-acetylphenyl)carboxamide; 1-N-(4-methylthiophenyl)carbamoyl-6,7-methylenedioxyoxindole-3-N-(2-fluoro-3-chlorophenyl)carboxamide; 1-N-(2,5-difluorophenyl)-carbamoyl-6,7-methylenedioxyoxindole-3-N-(3-chloro-5-trifluoromethylphenyl)carboxamide; 1-N-(2-furyl)-carbamoyl-6,7-methylenedioxyoxindole-3-N-(methyl-2-imidazolyl)carboxamide; 1-N-(2-thienyl)carbamoyl-6,7-methylenedioxyoxindole-3-N-(5-methyl-2-furyl)carboxamide; and 1-N-(cycloheptyl)carbamoyl-6,7-methylenedioxyoxindole-3-N-(cycloheptyl)carboxamide.

EXAMPLE 66

1-Carbamoyl-5-chloro-6-cyclohexyloxindole-3-N-(phenyl)carboxamide

To a solution of 2.92 g. (0.01 mole) of 1-carbamoyl-5-chloro-6-cyclohexyloxindole and 2.4 g. (0.024 mole) of triethylamine in 35 ml. of dimethylformamide at 0°–5° C. is added 1.43 g. (0.012 mole) of phenylisocyanate, and the reaction mixture allowed to stir for 3 hours. The mixture is poured into 350 ml. of 1N hydrochloric acid and allowed to stir for 20 minutes. The product is filtered, dried and recrystallized from ethyl acetate.

EXAMPLE 67

Using the procedure of Example 66 and starting with the requisite 1-carbamoyloxindole and appropriate isocyanate, the following compounds are prepared:

1-N-(n-hexyl)carbamoyl-5-chloro-6-cyclohexyloxindole-3-N-(2,4-difluorophenyl)carboxamide; 1-N-(cycloheptyl)carbamoyl-4-fluoro-6-cyclohexyloxindole-3-N-(4-acetylphenyl)carboxamide; 1-N-(2-thienyl)carbamoyl-4-chloro-6-cycloheptyloxindole-3-N-(2-methoxy-4-ethylphenyl)carboxamide; 1-N-(2-furyl)carbamoyl-4-chloro-6-cycloheptyloxindole-3-carboxamide; 1-carbamoyl-4-bromo-5-cyclopropyloxindole-3-N-(3,4-dimethoxyphenyl)carboxamide; 1-N-(t-butyl)-carbamoyl-4-methyl-6-cyclohexyloxindole-3-N-(2,4-dichlorophenyl)carboxamide; 1-carbamoyl-4-methoxy-6-cyclohexyl-3-N-(2,4-dichlorophenyl)carboxamide; 1-carbamoyl-4-methoxy-6-cyclohexyloxindole-3-N-(4-chlorophenyl)carboxamide; 1-N-(3-trifluorophenyl)carbamoyl-5-ethoxy-7-cyclopropyloxindole-3-N-(methylthiophenyl)carboxamide; 1-N-(4-methoxyphenyl)carbamoyl-6-methylthio-5-cyclopropyloxindole-3-N-(2-thienyl)carboxamide; 1-carbamoyl-6-n-propylthio-5-cyclopropyloxindole-3-N-(phenyl)carboxamide; and 1-N-(4-propionylphenyl)carbamoyl-5-cyclohexyl-7-fluorooxindole-3-N-(4-bromophenyl)carboxamide.

PREPARATION A

5-Chlorooxindole

To a stirred slurry of 100 g. (0.55 mol) of 5-chloroisatin in 930 ml. of ethanol was added 40 ml. (0.826 mol) of hydrazine hydrate, resulting in a red solution. The solution was heated under reflux for 3.5 hours, during which time a precipitate appeared. The reaction mixture was stirred overnight, and then the precipitate was recovered by filtration to give 5-chloro-3-hydrazonooxindole as a yellow solid, which was dried in a vacuum oven. The dried solid weighed 105.4 g.

The dried solid was then added portionwise, during 10 minutes, to a solution of 125.1 g. of sodium methoxide in 900 ml. of absolute ethanol. The resultant solution was heated under reflux for 10 minutes and then it was concentrated in vacuo to a gummy solid. The gummy solid was dissolved in 400 ml. of water and the aqueous solution thus obtained was decolorized with activated carbon and then poured into a mixture of 1 liter of water and 180 ml. of concentrated hydrochloric acid containing ice chips. A tan solid precipitated and it was cooled by filtration and washed thoroughly with water. The solid was dried and then it was washed with diethyl ether. Finally it was recrystallized from ethanol to give 48.9 g. of the title compound, m.p. 193°–195° C. dec.

In a similar manner 5-methyl-, 5-n-propyl- and 5-n-butylisatin are converted to the corresponding 5-substituted oxindoles.

PREPARATION B

4-Chlorooxindole and 6-chlorooxindole 1. 3-Chloro-isonitrosoacetanilide

To a stirred solution of 113.23 g. (0.686 mol) of chloral hydrate in 2 liters of water was added 419 g. (2.95 mol) of sodium sulfate, followed by a solution prepared from 89.25 g. (0.70 mol) of 3-chloroaniline, 62 ml. of concentrated hydrochloric acid and 500 ml. of water. A thick precipitate formed. To the reaction mixture was then added, with stirring, a solution of 155 g. (2.23 mol) of hydroxylamine in 500 ml. of water. Stirring was continued and the reaction mixture was warmed slowly and it was maintained between 60° and 75° C. for approximately 6 hours, during which time an additional 1 liter of water had been added to facilitate stirring. The reaction mixture was then cooled and the precipitate was recovered by filtration. The wet solid was dried to give 136.1 g. of 3-chloroisonitrosoacetanilide.

2. 4-Chloroisatin and 6-chloroisatin

To 775 ml. of concentrated sulfuric acid, preheated to 70° C., was added, with stirring 136 g. of 3-chloro-isonitrosoacetanilide at such a rate as to maintain the reaction medium at a temperature between 75° and 85° C. When all the solid had been added, the reaction mixture was heated at 90° C. for an additional 30 minutes. The reaction mixture was then cooled, and poured slowly onto ca 2 liters of ice, with stirring. Additional ice was added as necessary to maintain the temperature below room temperature. A red-orange precipitate formed which was recovered by filtration, washed with water and dried. The resultant solid was slurried in 2 liters of water, and then it was brought into solution by addition of ca 700 ml. of 3N sodium hydroxide. The solution was filtered, and then pH was adjusted to 8 with concentrated hydrochloric acid. At this point, 120 ml. of a mixture of 80 parts water and 20 parts concentrated hydrochloric acid was added. The solid which precipitated was recovered by filtration, washed with water and dried to give 50 g. of crude 4-chloroisatin. The filtrate from which the 4-chloroisatin had been recovered was further acidified to pH 0 using concentrated hydrochloric acid, whereupon a further precipitate formed. It was recovered by filtration, washed with water and dried, to give 43 g. of crude 6-chlorisatin.

The crude 4-chloroisatin was recrystallized from acetic acid to give 36.2 g. of material melting at 261°–262° C.

The crude 6-chloroisatin was recrystallized from acetic acid to give 36.2 g. of material melting at 261°–262° C.

3. 4-Chlorooxindole

To a stirred slurry of 43.3 g. of 4-chloroisatin in 350 ml. of ethanol was added 17.3 ml. of hydrazine hydrate, and then the reaction mixture was heated under reflux for 2 hours. The reaction mixture was cooled, and the precipitate was recovered by filtration to give 43.5 g. of 4-chloro-3-hydrazonooxindole, m.p. 235°–236° C.

To a stirred solution of 22 g. of sodium in 450 ml. of anhydrous ethanol was added, portionwise, 43.5 g. of 4-chloro-3-hydrazonooxindole, and the resulting solution was heated under reflux for 30 minutes. The cooled solution was then concentrated to a gum, which was dissolved in 400 ml. of water and decolorized using activated carbon. The resulting solution was poured onto a mixture of 1 liter of water and 45 ml. of concentrated hydrochloric acid. The precipitate which formed was recovered by filtration, dried and recrystallized from ethanol, giving 22.4 g. of 4-chlorooxindole, m.p. 216–218° C. dec.

4. 6-Chlorooxindole

Reaction of 36.2 g. of 6-chloroisatin with hydrazine hydrate followed by sodium ethoxide in ethanol, substantially according to B above, afforded 14.2 g. of 6-chlorooxindole, m.p. 196°–198° C.

In an analogous manner 4- and 6-fluoro- and bromooxindoles are prepared, as well as 7-fluorooxindole, 7-bromooxindole, 7-methyloxindole, 4,6-difluorooxindole, 4,7-dichlorooxindole, 5,7-difluorooxindole, 5-n-butyl-7-fluorooxindole, 7-cyclohexyloxindole and 7-cyclopropyloxindole.

PREPARATION C

5-Fluorooxindole

To a stirred solution of 11.1 g. (0.1 mol) of 4-fluoroaniline in 200 ml. of dichloromethane, at −60° to −65° C., was added, dropwise, a solution of 10.8 g. (0.1 mol) of t-butyl hypochlorite in 25 ml. of dichloromethane. Stirring was continued for 10 minutes at −60° to −65° C., and then was added, dropwise, a solution of 13.4 g. (0.1 mol) of ethyl 2-(methylthio)acetate in 25 ml. of dichloromethane. Stirring was continued at −60° C. for 1 hour and then was added, dropwise, at −60° C. to −65° C., a solution of 11.1 g. (0.11 mol) of triethylamine in 25 ml. of dichloromethane. The cooling bath was removed, and when the reaction mixture had warmed to room temperature, 100 ml. of water was added. The phases were separated, and the organic phase was washed with saturated sodium chloride solution, dried ($Na_2SO_4$) and evaporated in vacuo. The residue was dissolved in 350 ml. of diethyl ether, to which was added 40 ml. of 2N hydrochloric acid. This mixture was stirred at room temperature overnight. The phases were separated and the ether phase was washed with water, followed saturated sodium chloride. The dried ($Na_2SO_4$) ether phase was evaporated in vacuo to give 17 g. of an orange-brown solid which was triturated under isopropyl ether. The solid was then recrystallized from ethanol, to give 5.58 g. of 5-fluoro-3-methylthiooxindole, m.p. 151.5°–152.5° C.

Anal. Calcd. for $C_9H_8ONFS$: C, 54.80; H, 4.09; N, 7.10%. Found: C, 54.74; H, 4.11; N, 7.11%.

A sample of the above 5-fluoro-3-methylthiooxindole (986 mg. 5.0 mmole) was added to 2 teaspoonsful of Raney nickel under 50 ml. of absolute ethanol, and then the reaction mixture was heated under reflux for 2 hours. The catalyst was removed by decantation and was washed with absolute ethanol. The combined ethanol solutions were evaporated in vacuo and the residue was dissolved in dichloromethane. The dichloromethane solution was dried (Na$_2$SO$_4$) and evaporated in vacuo to give 475 mg. of 5-fluorooxindole, m.p. 121°–134° C.

PREPARATION D

5-Methoxyoxindole

5-Methoxyoxindole was prepared from 4-methoxyaniline in a manner similar to the procedure of Preparation C, except that the initial chlorination step was carried out using a solution of chlorine gas in dichloromethane in place of t-butyl hypochlorite. The title product melted at 150.5°–151.5° C.

PREPARATION E

6-Chloro-5-fluorooxindole

To 130 ml. of toluene was added, with stirring, 24.0 g. (0.165 mole) of 3-chloro-4-fluoroaniline and 13.5 ml. (0.166 mole) of pyridine. The resulting solution was cooled to ca 0° C. and 13.2 ml. (0.166 mole) of 2-chloroacetyl chloride was added. The reaction mixture was stirred at room temperature for 5 hours and then it was extracted twice with 100 ml. of 1N hydrochloric acid, followed by 100 ml. of saturated sodium chloride solution. The resulting toluene solution was dried using magnesium sulfate, and then it was concentrated in vacuo to give 32.6 g. (88% yield) of N-(2-chloroacetyl)-3-chloro-4-fluoroaniline.

A 26.63 g. sample of the N-(2-chloro)-2-chloro-4-fluoroaniline was thoroughly mixed with 64 g. of anhydrous aluminum chloride, and the mixture was heated at 210°–230° C. for 8.5 hours. The reaction mixture was then poured onto a mixture of ice an 1N hydrochloric acid, with stirring. Stirring was continued for 30 minutes, and then the solid was collected by filtration (22.0 g.). The solid was dissolved in 1:1 ethyl acetate-hexane and chromatographed on 800 g. of silica gel. Elution of the column, followed by evaporation of the fractions, produced 11.7 g. of the N-(2-chloroacetyl)-3-chloro-4-fluoroaniline, followed by 3.0 g. of 6-chloro-5-fluorine-2-oxindole. The latter material was recrystallized from toluene to give 1.70 g. (7% yield) of the title compound, m.p. 196°–206° C. Analysis by NMR spectroscopy indicated that the product was contaminated by some 4-chloro-5-fluorooxindole. A second crop weighing 0.8 g. was obtained.

In a similar manner are prepared 5-fluoro-6-bromo, 5,6-dibromo, 5-fluoro-5-ethyl-, 5-methoxy-6-fluoro, 5-ethyl-6-methyl-5-methylthio-6-methoxy, dimethylthio-, 5-fluoro-6-methoxy-, 4-fluoro-6-ethylthio, 4-fluoro-6-chloro, 5-chloro-7-bromo, 5-chloro-6-fluoro- and 4-chloro-6-n-butylthiooxindole.

PREPARATION F

6-Bromooxindole

To 9.4 g. of sodium hydride was added 195 ml. of dimethyl sulfoxide, followed by the dropwise addition of 22.37 ml. of dimethylmalonate. At the end of the addition, the mixture was heated to 100° C. and maintained at that temperature for 40 minutes. At this point, 25 g. of 1,4-dibromo-2-nitrobenzene was added all at once. The reaction mixture was maintained at 100° C. for 4 hours and then it was added to 1.0 liter of saturated ammonium chloride solution. The resulting mixture was extracted with ethyl acetate and the extracts were washed with ammonium chloride solution, water and saturated sodium chloride. The dried (MgSO$_4$) solution was evaporated, and the residue was recrystallized from ethyl acetate-hexane to give 22.45 g. of dimethyl 2-(4-bromo-2-nitrophenyl)malonate.

A solution of 17.4 g. of dimethyl 2-(4-bromo-2-nitrophenyl)malonate and 4.6 g. of lithium chloride in 150 ml. of dimethyl sulfoxide was placed in an oil bath at 100° C. After 3 hours, the reaction mixture was cooled to room temperature and then it was poured into a mixture of 500 ml. of ethyl acetate and 500 ml. of saturated sodium chloride solution. The layers were separated and the aqueous layer was extracted with further ethyl acetate. The combined organic layers were washed with saturated sodium chloride solution, dried using sodium sulfate, and then evaporated in vacuo. The residue was chromatographed using silica gel as adsorbant and ethyl acetate-hexane mixture as eluant. This afforded 9.4 g. of methyl 2-(4-bromo-2-nitrophenyl)acetate.

To a solution of 7.4 g. of methyl 2-(4-bromo-2-nitrophenyl)acetate in 75 ml. of acetic acid was added 6.1 g. of iron powder. The reaction mixture was placed in an oil bath at 100° C. After 1 hour, the solvent was removed by evaporation in vacuo, and the residue was dissolved in 250 ml. of ethyl acetate. The solution was filtered, washed with saturated sodium chloride solution, dried using sodium sulfate decolorized using activated carbon, and evaporated in vacuo. This afforded 5.3 g. of 6-bromooxindole as a white crystalline solid, m.p. 213–14 214° C.

In like manner, starting with 1,4,5-trichloro-2-nitrobenzene, 5,6-dichlorooxindole was prepared m.p. 209°–210° C.

In a similar manner, starting with 2-chloro-3-nitroacetophenone and 2-chloro-3-nitrobenzophenone, 4-acetyloxindole and 4-benzoyloxindole can be prepared, respectively.

Again, using this procedure and starting with 2-chloro-3-(2-thenoyl)-1-nitrobenzene and 2-chloroo-3-(3-thenoyl)-1-nitrobenzene, 4-(2- and 3-thenoyl)oxindole can be prepared, respectively.

PREPARATION G

5-Bromooxindole

5-Bromooxindole is prepared according to the procedure described by Beckett et al., Tetrahedron, 24, 6093 (1968), as are 4, 5, 6 and 7-methoxy and 5-ethoxyoxindoles.

PREPARATION H

Trifluoromethyloxindoles

6-Trifluoromethyloxindole is prepared by the procedure described by Simet, J. Org. Chem., 28, 3580 (1963). 4, 5 and 7-Trifluoromethyloxindoles are synthesized by reduction of the corresponding isatins as described by Maginnity et al., J. Am. Chem. Soc., 73, 3579 (1951).

The procedure of Simet can be used to prepare 5-chloro-6-trifluoromethyl, 5-methyl-6-trifluoromethyl-, 5-fluoro-6-trifluoromethyl- and 4-methyl-6-trifluoromethyloxindole.

The procedure of Maginnity can be used to prepare 6-chloro-7-trifluoromethyl-, 7-methoxy-5-trifluoromethyl-, 6-methylthio-5-trifluoromethyl-, 6-n-propyl-4-trifluoromethyl-, 6-n-propylthio-4-trifluoromethyl-, 6-n-propoxy-4-trifluoromethyl-, 5-methyl-4-trifluoromethyl-, 7-bromo-5-trifluoromethyl-, 5-n-butyl-7-trifluoromethyl-, 5-methoxy-7-trifluoromethyl-, 5-bromo-7-trifluoromethyl-, 5-methylthio-7-trifluoromethyl- and 4-fluoro-7-trifluoromethyloxindole.

PREPARATION I

Alkylthiooxindoles

4-Methylthiooxindole and 6-methylthiooxindole are prepared according to the procedure of U.S. Pat. No. 4,006,161. 7-Methylthio and 7-n-butylthiooxindoles are prepared by using the same procedure starting with 2-methylthioaniline and 2-n-butylthioaniline, respectively. 5-n-Propylthiooxindole is prepared by the same synthetic route starting with 4-n-propylthioaniline.

PREPARATION J

6-Benzoyloxindole

J1. diethyl 2-nitro-4-benzoylphenylmalonate

To a solution of sodium ethoxide, formed by reacting 4.6 g. (0.2 mole) of sodium metal with 200 ml. of ethanol, at 0° C. was added 32 g. (0.2 mole) of diethyl malonate followed by 26.1 g. (0.1 mole) of 4-chloro-3-nitrobenzophenone. The mixture was allowed to stir at room temperature for 2 hours and was then poured into 400 ml. of ice cold 2N hydrochloric acid and 300 ml. of methylene chloride. The organic layer was separated, dried over magnesium sulfate and concentrated to an oil. The residual oil was induced to crystallize by trituration with hexane containing trace amounts of diisopropyl ether, 34.75 g., m.p. 68°–70° C. The sample was further purified by trituration with hot hexane-diisopropyl ether, 30.84 g. (80% yield).

Anal. Calcd. for $C_{20}H_{19}NO_7$: C, 62.3; H, 5.0; N, 3.6. Found: C, 62.3; H, 4.9; N, 3.6.

J2. 2-nitro-4-benzoylphenylacetic acid

A mixture of 14 g. (36.3 mmoles) of diethyl 2-nitro-4-benzoylphenylmalonate, 300 ml. of 4N hydrochloric acid and 300 ml. of dioxane was heated to reflux for 10 hours. The reaction mixture was concentrated in vacuo and the crude product was triturated with hot methylene chloride, 9.88 g. (95% yield), m.p. 168°–170° C.

Anal. Calcd. for $C_{15}H_{11}NO_5$: C, 63.2; H, 3.9; N, 4.9. Found: C, 62.9; H, 4.0; N, 4.9.

J3. ethyl 2-nitro-4-benzoylphenylacetate

To a solution of 13.8 g. (48.4 mmoles) of 2-nitro-4-benzoylphenylacetic acid in 150 ml. of 1,2-dimethoxyethane at 15° C. was added 5.87 g. (58.1 mmole) of triethylamine. After 5 minutes 5.75 g. (53.2 mmoles) of ethylchloroformate was added and the reaction mixture allowed to stir at 10° C. for 15 minutes. Ethanol (15 ml.) was added and the reaction subsequently was added to a mixture of diethyl ether and a saturated brine solution. The organic phase was separated, dried over magnesium sulfate and concentrated to an oil, which was induced to crystallize, 14.3 g. (94% yield), m.p. 61°–62° C.

Anal. Calcd. for $C_{17}H_{15}NO_5$: C, 65.2; H, 4.8; N, 4.5. Found: C, 65.0; H, 4.8; N, 4.3.

J4. ethyl 2-amino-4-benzoylphenylacetate

To a solution of 14 g. (44.7 mmoles) of ethyl 2-nitro-4-benzoylphenylacetate in 225 ml. of ethanol was added 15 g. of wet Raney nickel and the mixture heated to reflux for 1.5 hours. The mixture was filtered and the filtrate concentrated to give a residual oil which was induced to crystallize by trituration with diethyl ether, 7.9 g., m.p. 150°–152° C.

The NMR spectrum (CDCl$_3$) showed absorption at 1.24 (t, J=7 Hz, CH$_3$), 3.61 (s, CH$_2$), 4.13 (q, J=7 Hz, CH$_2$) and 7.0–7.9 (m, ArH) ppm.

J5. 6-benzoyloxindole

A mixture of 5.0 (17.6 mmoles) of ethyl 2-amino-4-benzoylphenylacetate and 999 mg. of p-toluenesulfonic acid in 300 ml. of toluene was heated to 110° C. for 5 minutes. The reaction was cooled and added to a mixture of methylene chloride and a saturated sodium bicarbonate solution. The organic phase was separated, dried and concentrated to a solid, 3.68 g. (88% yield), m.p. 206°–208° C.

In a similar manner, starting with the appropriate reagent 6-n-butyryloxindole, 4-chloro-6-benzoyloxindole, 4-fluoro-6-acetyloxindole, 4-methoxy-6-benzoyloxindole, 4-methoxy-6-butyryloxindole, 6-(2-thenoyl)oxindole, 6-(3-thenoyl)oxindole, 4-methyl-6-(2-thenoyl)oxindole, 4-methylthio-6-(3-thenoyl)oxindole and 4-fluoro-6-(2-thenoyl)oxindole are prepared.

PREPARATION K

7-Acetyloxindole

K1. 7-acetylindoline

To a solution of 47.35 g. (0.5 mole) of boron tribromide in 300 ml. of toluene at 0° C. was added dropwise a solution of 50 g. (0.42 mole) of indoline and 22.39 g. (0.546 mole) of acetonitrile in 200 ml. of toluene. After stirring for 10 minutes 67.2 g. (0.5 mole) of aluminum chloride was added in portions. The resulting reaction mixture was heated to reflux for 66 hours, cooled to 5° C. and treated with 80 ml. of water and 330 ml. of 2N hydrochloric acid. The resulting mixture was heated to reflux for 2.5 hours, cooled and filtered. The filtrate was set aside and the solids suspended in 500 ml. of water and treated with 2N sodium hydroxide solution until basic. The basic mixture was extracted (2×200 ml.) with methylene chloride and the organic phase separated, dried and concentrated to a solid, 17.2 g. The filtrate which was set aside was made basic with 4N aqueous sodium hydroxide and extracted with methylene chloride. The organic phase was separated, dried and concentrated to a solid, 21.8 g. The combined solids were recrystallized from hexane, 30 g., m.p. 83°–85° C.

K2. 7-acetylindole

To 30 g. (0.186 mole) of 7-acetylindoline in 415 ml. of methylene chloride was added 48.5 g (0.56 mole) of manganese dioxide and the mixture refluxed through a soxhlet filled with 4A molecular sieves for 22 hours. The mixture was cooled and an additional 48.5 g. of manganese dioxide was added. Fresh molecular sieves were added and the refluxing continued for 5 hours. The same amount of manganese dioxide and molecular sieves were added again and the refluxing was continued for one hour. The mixture was filtered and the filtrate concentrated to dryness. The residue was triturated with hexane and filtered, 22.57 g. (76% yield), m.p. 65°–66° C.

K3. 7-acetyloxindole

To a solution of 12.57 g. (79 mmoles) of 7-acetylindole in 187 ml. of methylene chloride was added 11.07 g. (82.9 mmoles) of N-chlorosuccinimide and the reaction allowed to stir at room temperature for 2 hours.

The solvent was removed in vacuo and the residue treated with 155 ml. of acetic acid and heated to 80° C. Phosphoric acid (80 ml.) was added and the reaction mixture heated to reflux for 9 hours. The mixture was cooled, the acetic acid removed under vacuum and the residue poured into 500 ml. of ice and water. The product was extracted with methylene chloride, 11.91 g. (65% yield), 174°–175° C.

Starting with the appropriate reagents and following the procedure of Preparation K, 7-propionyloxindole, 7-benzoyloxindole, 7-(2-thenoyl)oxindole, 7-(3-thenoyl)oxindole, 5-methyl-7-acetyloxindole, 5-methylthio-7-acetyloxindole, 5-fluoro-7-benzoyloxindole and 5-bromo-7-(2-thenoyl)oxindole are prepared.

PREPARATION L

5-Benzoyloxindole

To 4.87 ml. (0.042 mole) of benzoyl chloride and 27 g. (0.202 mole) of aluminum chloride in 100 ml. of carbon disulfide was added 4.4 g. (0.033 mole) of oxindole and the reaction mixture heated to reflux for 3 hours. The solvent was decanted and the residue added to 300 ml. of water and allowed to stir for 20 minutes. The product was filtered, dried and recrystallized from methanol, 2.0 g., m.p. 203°–205° C.

Using a similar procedure and starting with the requisite reagents, 5-acetyloxindole, 5-propionyloxindole, 5-(2-thenoyl)oxindole, 5-(3-thenoyl)oxindole, 4-methyl-5-acetyloxindole, 4-chloro-5-acetyloxindole and 7-methyl-5-benzoyloxindole are prepared.

PREPARATION M

5,6-Methylenedioxyindole 5,6-Methylenedioxyoxindole can be prepared via the reduction of methyl 2-nitro-4,5-methylenedioxyphenylacetate according to the procedure of McEvoy et al., *J. Org. Chem.*, 38, 3350 (1973). By a similar procedure, starting with the appropriate methyl 2-nitromethylenedioxyphenylacetate, 4,5-methylenedioxyoxindole and 6,7-methylenedioxyoxindole are prepared.

PREPARATION N

Cycloalkyloxindoles

5-Cyclohexyl- and 5-cycloheptyloxindoles can be prepared by reaction of 5-cyclohexyl- and 5-cycloheptylisatin, respectively, with hydrazine hydrate followed by sodium methoxide in ethanol, according to the procedure of Preparation A. 5-Cyclohexyl- and 5-cycloheptylisatins can be prepared from 4-cyclohexylaniline and 4-cycloheptylaniline, respectively, by treatment with chloral hydrate and hydroxylamine, followed by cyclization with sulfuric followed by cyclization with sulfuric acid according to Preparation B1 and B2.

4-Cyclohexyl- and 6-cyclohexyloxindoles can be prepared by the procedure of Preparation B, starting with 3-cyclohexylaniline. Similarly, 4- and 6-cyclopentyl- and cyclobutyloxindoles can be prepared by this procedure as well as 5-chloro-6-cyclohexyl-, 4-fluoro-6-cyclohexyl-, 4-chloro-6-cycloheptyl-, 4-bromo-5-cyclopropyl-, 4-methoxy-6-cyclohexyl-, 5-ethoxy-7-cyclopropyl-, 6-methylthio-5-cyclopropyl-, 6-n-propyl-5-cyclopropyl- and 7-fluoro-5-cyclohexyloxindole.

PREPARATION O

Nitrooxindoles

5-Nitrooxindole can be prepared according to the procedure of Sumptor et al., *J. Am. Chem. Soc.*, 67, 499 (1945).

The procedure of Preparation A is employed to prepare 7-nitrooxindole starting with 2-nitroaniline as well as 4- and 6-nitroaniline, starting with 3-nitroaniline.

The procedure of Preparation A is also employed in the synthesis of 5-nitro-6-fluoro-, 4-fluoro-5-nitro-, 4-methyl-5-nitro, 4-chloro-5-nitro- and 5-fluoro- 6-nitrooxindole.

PREPARATION P

The procedure described in U.S. Pat. No. 3,882,236 can be employed in the preparation of 4-methyloxindole, 4-ethyloxindole, 6-methyloxindole, 6-i-propyloxindole, 4-chloro-5-methyloxindole, 6-methoxy-7-methyloxindole, 5-ethoxy-7-methyloxindole and 5-n-butoxy-7-methyloxindole.

PREPARATION Q

1-Carbamoyloxindole

To a slurry of 2-oxindole (13.3 g., 0.10 mole) in toluene (150 ml.) was added chlorosulfonylisocyanate (15.6 g., 0.11 mole) and the reaction mixture heated on a steam bath for ten minutes (a clear solution formed within about three minutes followed almost immediately by formation of a precipitate). It was then cooled in an ice bath for 30 minutes, the solid filtered off and air dried.

The thus obtained chlorosulfonamido intermediate was added to a 2:1 mixture of acetic acid/water (240 ml.) and the resulting slurry heated on a steam bath for ten minutes. It was cooled in an ice bath and the off white solid which formed filtered off and air dried. Concentration of the mother liquor to a slush and filtration thereof gave 1.2 g. of product. The combined solids was recrystallized from about 250 ml. of ethanol; yield=11.48 g., m.p. 178°–180° C.

This procedure can be used to prepare the unsubstituted ($R_2$=H) 1-carbamoyloxindoles employed as intermediates to the final products.

PREPARATION R

1-N-i-Propylcarbamoyloxindole

To a stirred suspension of 5.0 g. (37.6 mmole) of 2-oxindole in 50 ml. of toluene was added 8.0 g. (94.0 mmole) of isopropyl isocyanate, and the mixture was heated under reflux for 6 hours. The reaction mixture was allowed to cool and then it was stirred at room temperature overnight. The solvent was removed by evaporation in vacuo, and the residue was dissolved in hot cyclohexane. The solution was allowed to cool and the solid was collected by filtration, giving 7.0 g. of the title compound, m.p. 84°–85.5° C., as pink crystals.

This procedure can be employed in the synthesis of N-substituted-1-carbamoyloxindoles used as intermediates to the final products.

PREPARATION S

Methyl 1-N-(phenyl)carbamoyl-5-chlorooxindole-3-carboxylate

To 6.0 g. (0.027 mole) of methyl 5-chlorooxindole-3-carboxylate in 200 ml. of toluene was added 5.25 ml. (0.048 mole) of phenylisocyanate and the resulting reaction mixture heated to reflux overnight. The reaction mixture was cooled and diluted with petroleum ether to give, after filtration and drying, 2.0 g. of the desired product.

This procedure can be used in the synthesis of alkyl 1-N-substituted carbamoyloxindole-3-carboxylates used as intermediates to the final products.

I claim:

1. A 1,3-dicarboxamidooxindole compound of the formula

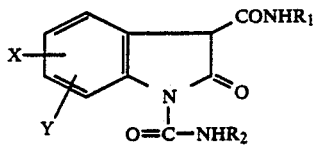

and a pharmaceutically-acceptable base salt thereof, wherein
  X is selected from the group consisting of hydrogen, fluoro, chloro, bromo, alkyl having one to four carbon atoms, alkylthio having one to four carbon atoms, alkoxy having one to four carbon atoms, cycloalkyl having three to six carbon atoms, nitro, trifluoromethyl, acetyl, propionyl, butyryl, benzoyl and thenoyl;
  Y is selected from the group consisting of hydrogen, fluoro, chloro, bromo, alkyl having one to four carbon atoms, alkoxy having one to four carbon atoms and alkylthio having one to four carbon atoms;
  X and Y when taken are selected from the group consisting of 4,5-, 5,6- and 6,7-methylene dioxy; and
  $R_1$ and $R_2$ are each selected from the group consisting of hydrogen, alkyl having one to six carbon atoms, cycloalkyl having three to seven carbon atoms, and groups of the formula

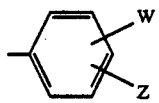

wherein W is selected from the group consisting of hydrogen, fluoro, chloro, bromo, alkyl having one to four carbon atoms, alkylthio having one to four carbon atoms, alkoxy having one to four carbon atoms, trifluoromethyl, acetyl, propionyl, and cycloalkyl having three to six carbon atoms and Z is selected from the group consisting of hydrogen, fluoro, chloro, bromo, alkyl having one to four carbon atoms, alkoxy having one to four carbons and alkylthio having one to four carbon atoms.

2. A compound of claim 1, wherein $R_1$ is a group of the formula

wherein W is selected from the group consisting of hydrogen, fluoro, chloro, bromo, alkyl having one to four carbon atoms, alkylthio having one to four carbon atoms, alkoxy having one to four carbon atoms, trifluoromethyl, acetyl, propionyl and cycloalkyl having three to six carbon atoms and Z is selected from the group consisting of hydrogen, fluoro, chloro, bromo, alkyl having one to four carbon atoms, alkoxy having one to four carbon atoms and alkylthio having one to four carbon atoms; and $R_2$ is hydrogen.

3. The compound of claim 2, wherein $R_1$ is 2-chlorophenyl, X is 5-chloro and Y is hydrogen.

4. The compound of claim 2, wherein $R_1$ is 2,4-dichlorophenyl, X is 5-chloro and Y is hydrogen.

5. The compound of claim 2, wherein $R_1$ is 4-ethylphenyl, X is 5-chloro and Y is hydrogen.

6. The compound of claim 2, wherein $R_1$ is 2,4-dichlorophenyl and X and Y are each hydrogen.

7. The compound of claim 2, wherein $R_1$ is 2,4-dichlorophenyl, X is 5-chloro and Y is 6-chloro.

8. The compound of claim 2, wherein $R_1$ is 3-trifluoromethylphenyl, X is 5-chloro and Y is hydrogen.

9. The compound of claim 2 wherein $R_1$ is 4-chlorophenyl, X is 6-trifluoromethyl and Y is hydrogen.

10. The compound of claim 2, wherein $R_1$ is phenyl, X is 5-chloro and Y is hydrogen.

11. A method of treating an inflammatory disease in a mammalian subject, which comprises administering to said mammalian subject an inflammatory disease treating amount of a compound selected from claim 1.

12. A pharmaceutical composition, which comprises a pharmaceutically-acceptable carrier and a compound selected from claim 1, and wherein the weight-ratio of the pharmaceutically-acceptable carrier to said compound is in the range of from 1:4 to 20:1.

* * * * *